US012618842B2

(12) United States Patent
Tateno et al.

(10) Patent No.: US 12,618,842 B2
(45) Date of Patent: May 5, 2026

(54) CANCER TEST METHOD

(71) Applicants: NATIONAL INSTITUTE OF ADVANCED INDUSTRIAL SCIENCE AND TECHNOLOGY, Tokyo (JP); UNIVERSITY OF TSUKUBA, Tsukuba (JP)

(72) Inventors: Hiroaki Tateno, Tsukuba (JP); Tatsuya Oda, Tsukuba (JP); Osamu Shimomura, Tsukuba (JP)

(73) Assignees: NATIONAL INSTITUTE OF ADVANCED INDUSTRIAL SCIENCE AND TECHNOLOGY, Tokyo (JP); UNIVERSITY OF TSUKUBA, Tsukuba (JP)

( * ) Notice: Subject to any disclaimer, the term of this patent is extended or adjusted under 35 U.S.C. 154(b) by 995 days.

(21) Appl. No.: 17/717,764

(22) Filed: Apr. 11, 2022

(65) Prior Publication Data

US 2022/0236275 A1 Jul. 28, 2022

Related U.S. Application Data

(63) Continuation of application No. PCT/JP2020/038300, filed on Oct. 9, 2020.

(30) Foreign Application Priority Data

Oct. 11, 2019 (JP) ................................. 2019-187197

(51) Int. Cl.
| | |
|---|---|
| *G01N 33/574* | (2006.01) |
| *G01N 33/543* | (2006.01) |
| *G01N 33/548* | (2006.01) |

(52) U.S. Cl.
CPC ..... *G01N 33/57438* (2013.01); *G01N 33/548* (2013.01); *G01N 2333/4724* (2013.01); *G01N 2400/02* (2013.01)

(58) Field of Classification Search
CPC ........... G01N 33/57438; G01N 33/548; G01N 2333/4724; G01N 2400/02;
(Continued)

(56) References Cited

U.S. PATENT DOCUMENTS

| | | | |
|---|---|---|---|
| 6,596,476 B1 * | 7/2003 | Lesniewski | ............. C12Q 1/70 435/5 |
| 2014/0154713 A1 | 6/2014 | Mizuno et al. | |

(Continued)

FOREIGN PATENT DOCUMENTS

| | | |
|---|---|---|
| JP | 2020-146027 A | 9/2020 |
| WO | WO 2012/173002 A1 | 12/2012 |

(Continued)

OTHER PUBLICATIONS

Tateno, Hiroaki, et al. "Development of a practical sandwich assay to detect human pluripotent stem cells using cell culture media." Regenerative Therapy 6 (2017): 1-8. (Year: 2017).*

(Continued)

*Primary Examiner* — Gregory S Emch
*Assistant Examiner* — Christopher Evans
(74) *Attorney, Agent, or Firm* — Birch, Stewart, Kolasch & Birch, LLP

(57) ABSTRACT

The present invention relates to a method for analyzing a biological sample obtained from a subject, comprising analyzing components contained in a biological sample by an assay using a first molecule selected from the group consisting of a molecule binding to a sugar chain bindable with BC2LCN, a molecule binding to SerpinA3, and a molecule binding to Gal3BP, and a second molecule that is BC2LCN.

4 Claims, 20 Drawing Sheets

(58) Field of Classification Search
  CPC ..... G01N 2333/8121; G01N 33/57488; G01N 2333/47; G01N 2333/8125; G01N 33/574; G01N 33/543
  See application file for complete search history.

(56) References Cited

U.S. PATENT DOCUMENTS

| | | |
|---|---|---|
| 2015/0104816 A1 | 4/2015 | Noda et al. |
| 2015/0376568 A1 | 12/2015 | Tateno et al. |
| 2018/0250360 A1 | 9/2018 | Tateno et al. |
| 2020/0123222 A1 | 4/2020 | Tateno et al. |

FOREIGN PATENT DOCUMENTS

| | | |
|---|---|---|
| WO | WO 2014/126146 A1 | 8/2014 |
| WO | WO 2017/061449 A1 | 4/2017 |
| WO | WO 2018/190357 A1 | 10/2018 |

OTHER PUBLICATIONS

Ney, Jasmin Teresa, et al. "Podocalyxin-like protein 1 expression is useful to differentiate pancreatic ductal adenocarcinomas from adenocarcinomas of the biliary and gastrointestinal tracts." Human pathology 38.2 (2007): 359-364. (Year: 2007).*
Harlow, E. and Lane, D., Antibodies: A Laboratory Manual (1988) Cold Spring Harbor Laboratory Press, Cold Spring Harbor, NY (Year: 1988).*
Lederman, Seth, et al. "A single amino acid substitution in a common African allele of the CD4 molecule ablates binding of the monoclonal antibody, OKT4." Molecular immunology 28.11 (1991): 1171-1181. (Year: 1991).*
Brown et al., Tolerance of single, but not multiple, amino acid replacements in antibody VH CDR 2: a means of minimizing B cell wastage from somatic hypermutation? J Immunol. May 1, 1996; 156(9):3285-91. PMID: 8617951. (Year: 1996).*
Colman, Peter M. "Effects of amino acid sequence changes on antibody-antigen interactions." Research in immunology 145.1 (1994): 33-36. (Year: 1994).*
Nie, Song, et al. "Glycoprotein biomarker panel for pancreatic cancer discovered by quantitative proteomics analysis." Journal of proteome research 13.4 (2014): 1873-1884. (Year: 2014).*
Chinese Office Action and Search Report for corresponding Chinese Application No. 202080071169.X, dated Nov. 16, 2024, with an English translation.
Extended European Search Report for corresponding European Application No. 20873535.7, dated Oct. 25, 2022.
Läubli et al., "Lectin Galactoside-binding Soluble 3 Binding Protein (LGALS3BP) Is a Tumor-associated Immunomodulatory Ligand for CD33-related Siglecs," Journal of Biological Chemistry, vol. 289, No. 48, 2014, pp. 33481-33491.
Zeng et al., "Lung Cancer Serum Biomarker Discovery Using Glycoprotein Capture and Liquid Chromatography Mass Spectrometry," Journal of Proteome Research, vol. 9, 2010, pp. 6440-6449.
International Preliminary Report on Patentability and Written Opinion of the International Searching Authority (Forms PCT/IB/326, PCT/IB/373, and PCT/ISA/237) for International Application No. PCT/JP2020/038300, dated Apr. 21, 2022, with an English translation.
Kimyo et al., "Development of new clinical markers using serum glycoproteins-linked sugar chains," The Official Journal of Japanese Society of Laboratory Medicine, vol. 62, 2014, p. 140, 1 page total.
Koths et al., "Cloning and Characterization of a Human Mac-2-biding Protein, a New Member of the Superfamily Defined by the Macrophage Scavenger Receptor Cysteine-rich Domain," The Journal of Biological Chemistry, vol. 268, No. 19, 1993, pp. 14245-14249.
Nie et al., "Glycoprotein Biomarker Panel for Pancreatic Cancer Discovered by Quantitative Proteomics Analysis," Journal of Proteome Research, vol. 13, 2014, pp. 1873-1884.
Šulák et al., "A TNF-like Trimeric Lectin Domain from *Burkholderia cenocepacia* with Specificity for Fucosylated Human Histo-Blood Group Antigens," Structure, vol. 18, 2010, pp. 59-72.
Singapore Written Opinion for corresponding Singapore Application No. 11202203679X, dated Jun. 26, 2024.
Japanese Office Action for corresponding Japanese Application No. 2021-551720, dated Dec. 24, 2024, with English translation.
Chinese Office Action for corresponding Chinese Application No. 202080071169.X, dated Apr. 10, 2025, with English translation.
Korean Office Action for corresponding Korean Application No. 10-2022-7012018, dated Dec. 18, 2024, with English translation.
European Communication pursuant to Article 94(3) EPC for corresponding European Application No. 20 873 535.7, dated Jan. 23, 2026.

* cited by examiner rBC2LCN-rBC2LCN rBC2LCN-SerpinA3 ANTIBODY

HISTOLOGICAL STAINING OF PANCREATIC TISSUES

Scale bar: 100 μm

*, COMPARISON WITH AVERAGE VALUE OF normal AND Wilcoxon-Mann-Whitney assay

FIG. 11

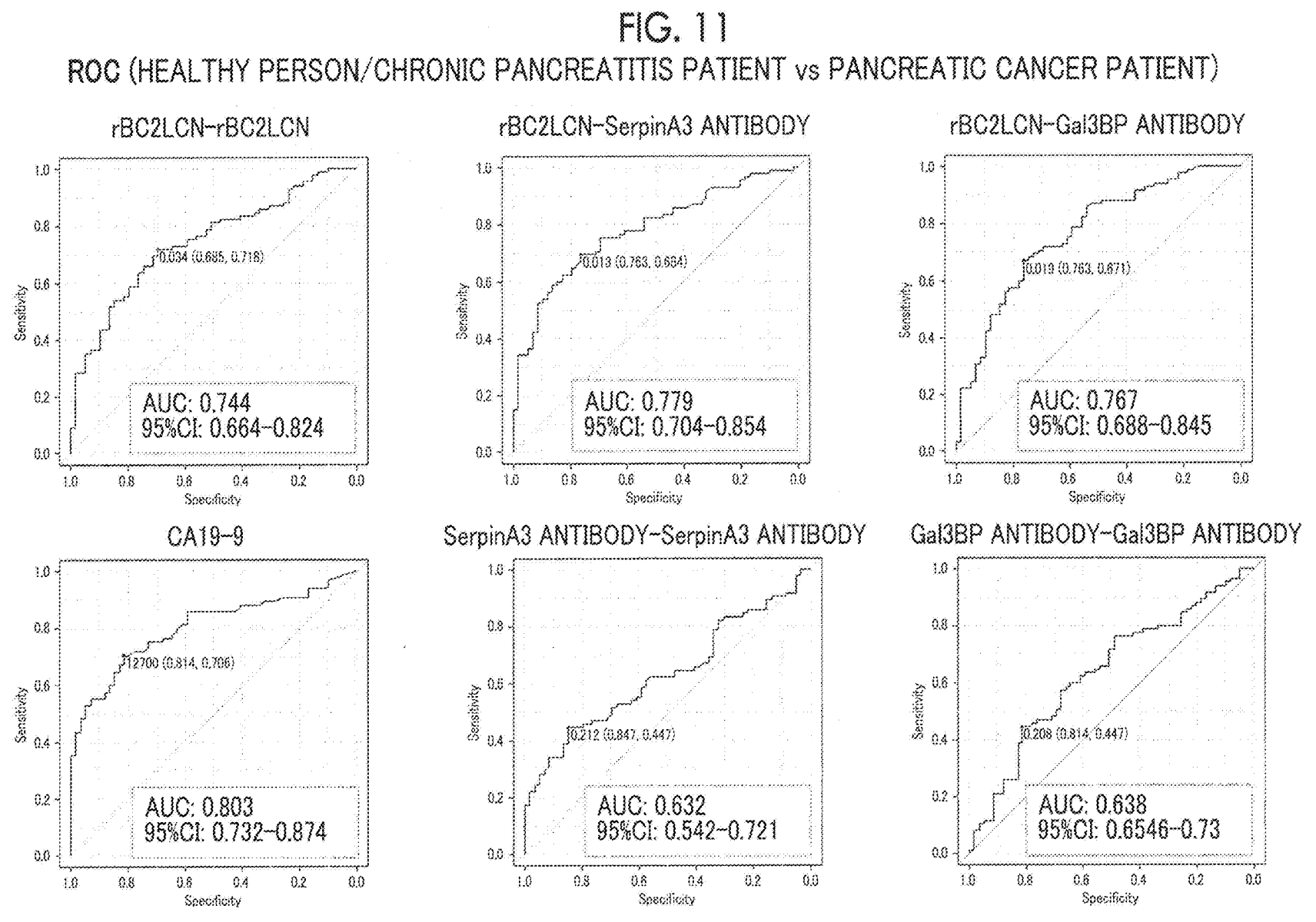

ROC (HEALTHY PERSON/CHRONIC PANCREATITIS PATIENT vs PANCREATIC CANCER PATIENT)

rBC2LCN-rBC2LCN
AUC: 0.744
95%CI: 0.664-0.824 rBC2LCN-SerpinA3 ANTIBODY
AUC: 0.779
95%CI: 0.704-0.854 rBC2LCN-Gal3BP ANTIBODY
AUC: 0.767
95%CI: 0.688-0.845

CA19-9
AUC: 0.803
95%CI: 0.732-0.874

SerpinA3 ANTIBODY-SerpinA3 ANTIBODY
AUC: 0.632
95%CI: 0.542-0.721

Gal3BP ANTIBODY-Gal3BP ANTIBODY
AUC: 0.638
95%CI: 0.546-0.73 rBC2LCN-SerpinA3 ANTIBODY rBC2LCN-SerpinA3 ANTIBODY

1 POD: 1 DAY AFTER OPERATION

7 POD: 7 DAYS AFTER OPERATION

30 POD: 30 DAYS AFTER OPERATION

CANCER TEST METHOD

CROSS-REFERENCE TO RELATED APPLICATIONS

This application is a Continuation of PCT International Application No. PCT/JP2020/038300, filed on Oct. 9, 2020, which claims priority under 35 U.S.C. § 119(a) to Japanese Patent Application No. 2019-187197, filed on Oct. 11, 2019. Each of the application(s) is hereby expressly incorporated by reference, in its entirety, into the present application.

TECHNICAL FIELD

The present invention relates to a cancer test method and a test kit for the same.

BACKGROUND ART

BC2LCN is a glycoprotein, that is, a kind of lectin, and according to previous reports, it has been revealed that BC2LCN has affinity for glycoprotein sugar chains H-type 1 (Fucα1-2Galβ1-3GlcNAc) and H-type 3 (Fucα1-2Galβ1-3GalNAc), and can thus be used as a probe for detecting an undifferentiated marker of human ES cells or iPS cells that express a podocalyxin having an H-type 3 sugar chain (Patent Literature 1). In addition, according to previous reports, it has been revealed that BC2LCN strongly binds to a cancer tissue and can thus be used as a probe for detecting a cancer marker (Patent Literature 2). According to Patent Literature 2, the presence of a protein recognized by BC2LCN and keratan sulfate in blood components of some cancer patients have been confirmed by a sandwich assay with BC2LCN and an antibody binding to keratan sulfate.

SerpinA3 is also referred to as an α1-antichymotrypsin and is known to be associated with diseases such as some tumors. SerpinA3 has been developed as a blood test marker (Non-Patent Literature 1).

Gal3BP is also referred to as LGAL3SBP or MAC-2-BP, and is found at high concentrations in the sera of patients with a breast cancer, a lung cancer, a rectal colorectal cancer, an ovarian cancer, and an endometrial cancer (Non-Patent Literature 2).

CITATION LIST

Patent Literature

Patent Literature 1: WO2014/126146A
Patent Literature 2: WO2017/061449A

Non-Patent Literature

Non-Patent Literature 1: Nie, S. et al., J. Proteome Res. 13: 1873-1884, 2014
Non-Patent Literature 2: Koths, K. et al., J. Biol. Chem. 268: 14245-14249, 1993

SUMMARY OF INVENTION

The present invention relates to a cancer test method and a test kit for the same.

According to the present invention, the following inventions are provided.

(1) A method for analyzing a blood sample obtained from a subject, comprising:

analyzing a blood component contained in a blood sample by a sandwich assay or an immunochromatographic assay, using a first molecule selected from the group consisting of BC2LCN, an antibody binding to SerpinA3, and an antibody binding to Gal3BP, and a second molecule that is BC2LCN.

(2) The method as described in (1),
in which the first molecule is an antibody binding to SerpinA3.

(3) The method as described in (1),
in which the first molecule is an antibody binding to Gal3BP.

(4) The method as described in (1),
in which the first molecule is BC2LCN.

(5) The method as described in any one of (1) to (4),
in which the subject has a cancer or has a potential to have the cancer.

(6) The method as described in (5),
in which the subject has a pancreatic cancer or has a potential to have the pancreatic cancer.

(7) The method as described in (6),
in which the subject has a stage I or II pancreatic cancer or has a potential to have the stage I or II pancreatic cancer.

(8) A kit for a sandwich assay or an immunochromatographic assay, comprising a first molecule selected from the group consisting of BC2LCN, an antibody binding to SerpinA3, and an antibody binding to Gal3BP, and a second molecule that is BC2LCN,
in which the kit can be used to measure an amount of a glycoprotein in a blood sample of a subject, using the first molecule and the second molecule.

(9) The kit as described in (8),
in which the first molecule is an antibody binding to SerpinA3 and a protein portion of the glycoprotein is SerpinA3.

(10) The kit as described in (8),
in which the first molecule is an antibody binding to Gal3BP and a protein portion of the glycoprotein is Gal3BP.

(11) The kit as described in (8), comprising:
a second molecule that is immobilized BC2LCN; and
a first labeled molecule selected from the group consisting of labeled BC2LCN, an antibody binding to labeled SerpinA3, and an antibody binding to labeled Gal3BP.

(12) The kit as described in any one of (8) to (11),
in which the kit is used for detecting a cancer.

(13) The kit as described in (12),
in which the cancer is a cancer selected from the group consisting of a pancreatic cancer and a colorectal cancer.

(14) The kit as described in (13),
in which the cancer is a stage I or II pancreatic cancer.

(15) A method for predicting whether or not a subject is a cancer, comprising carrying out the method as described in (1) to (7).

(16) A method for analyzing a blood sample obtained from a subject, comprising:
analyzing the presence or absence or the concentration of a blood component in a blood sample,
in which the blood component is a component selected from the group consisting of a component that can simultaneously bind to two BC2LCN's, SerpinA3 bindable with BC2LCN, and Gal3BP bindable with BC2LCN.

According to the present invention, the following inventions may also be provided.

(1A) A method for analyzing a biological sample obtained from a subject, comprising:

analyzing components contained in a biological sample by an assay using a first molecule selected from the group consisting of a molecule binding to a sugar chain bindable with BC2LCN, a molecule binding to SerpinA3, and a molecule binding to Gal3BP, and a second molecule that is BC2LCN.

(2A) The method as described in (1A),
in which the first molecule is an antibody binding to SerpinA3.

(3A) The method as described in (1A),
in which the first molecule is an antibody binding to Gal3BP.

(4A) The method as described in (1A),
in which the first molecule is BC2LCN.

(5A) The method as described in any one of (1A) to (4A),
in which the subject has a cancer or has a potential to have the cancer.

(6A) The method as described in (5A),
in which the subject has a pancreatic cancer or has a potential to have the pancreatic cancer.

(7A) The method as described in (6A),
in which the subject has a stage I or II pancreatic cancer or has a potential to the stage I or II pancreatic cancer.

(8A) A kit for a sandwich assay, a kit for an immuno-chromatographic assay, a kit for lectin electrophoresis, a kit for mass spectrometry, a kit for lectin affinity chromatography, or a kit for μTAS, comprising:

a first molecule selected from the group consisting of BC2LCN, a molecule binding to SerpinA3, and a molecule binding to Gal3BP; and
a second molecule that is a molecule binding to a sugar chain bindable with BC2LCN,
in which the kit can be used to measure an amount of a glycoprotein in a biological sample of a subject, using the first molecule and the second molecule.

(9A) The kit as described in (8A),
in which the first molecule is an antibody binding to SerpinA3 and a protein portion of the glycoprotein is SerpinA3.

(10A) The kit as described in (8A),
in which the first molecule is an antibody binding to Gal3BP and a protein portion of the glycoprotein is Gal3BP.

(11A) The kit as described in (8A), comprising:
a second molecule that is immobilized BC2LCN; and
a first labeled molecule selected from the group consisting of labeled BC2LCN, an antibody binding to labeled SerpinA3, and an antibody binding to labeled Gal3BP.

(12A) The kit as described in any one of (8A) to (11A),
in which the kit is used for detecting a cancer.

(13A) The kit as described in (12A),
in which the cancer is a pancreatic cancer.

(14A) The kit as described in (13A),
in which the cancer is a stage I or II pancreatic cancer.

(15A) A method for predicting whether or not a subject is a cancer, comprising carrying out the method as described in any one of (1A) to (7A).

(16A) A method for detecting a specific component in a biological sample obtained from a subject, in which the specific component is a component selected from the group consisting of a component that can simultaneously bind to two BC2LCN's, SerpinA3 bindable with BC2LCN, and Gal3BP bindable with BC2LCN.

(17A) A method comprising separating one or more components selected from the group consisting of a component that can simultaneously bind to two BC2LCN's, SerpinA3, and Gal3BP from a biological sample obtained from a subject.

(18A) The method as described in (17A),
in which the subject is a subject having a pancreatic cancer or a subject having a potential to have the pancreatic cancer.

(19A) The method as described in (17A),
in which the pancreatic cancer is a stage I or II pancreatic cancer.

(20A) The method as described in any one of (17A) to (19A), further comprising measuring amounts of the separated components.

(21A) The method as described in (20A), further comprising comparing a cut off value with the amounts of the measured components.

(22A) The method as described in (21A),
in which the cut off value is a value equal to or more than an average value of amounts of components corresponding to the measured components in a healthy person, and is a value equal to or less than an average value of amounts of components corresponding to the measured components in a pancreatic cancer patient.

(23A) The method as described in any one of (17A) to (19A), further comprising detecting the separated components.

BRIEF DESCRIPTION OF DRAWINGS

FIG. 7 is an ROC curve showing a relationship between a sensitivity and a specificity in an evaluation system for detecting a pancreatic cancer, using a concentration of blood factors that can be simultaneously recognized by two molecules of BC2LCN, a concentration of SerpinA3 bindable with BC2LCN, a concentration of Gal3BP bindable with BC2LCN, and a concentration of SerpinA3 measured using two different anti-SerpinA3 antibodies in blood samples of pancreatic cancer patients and healthy persons as an indicator.

Figure 8A:
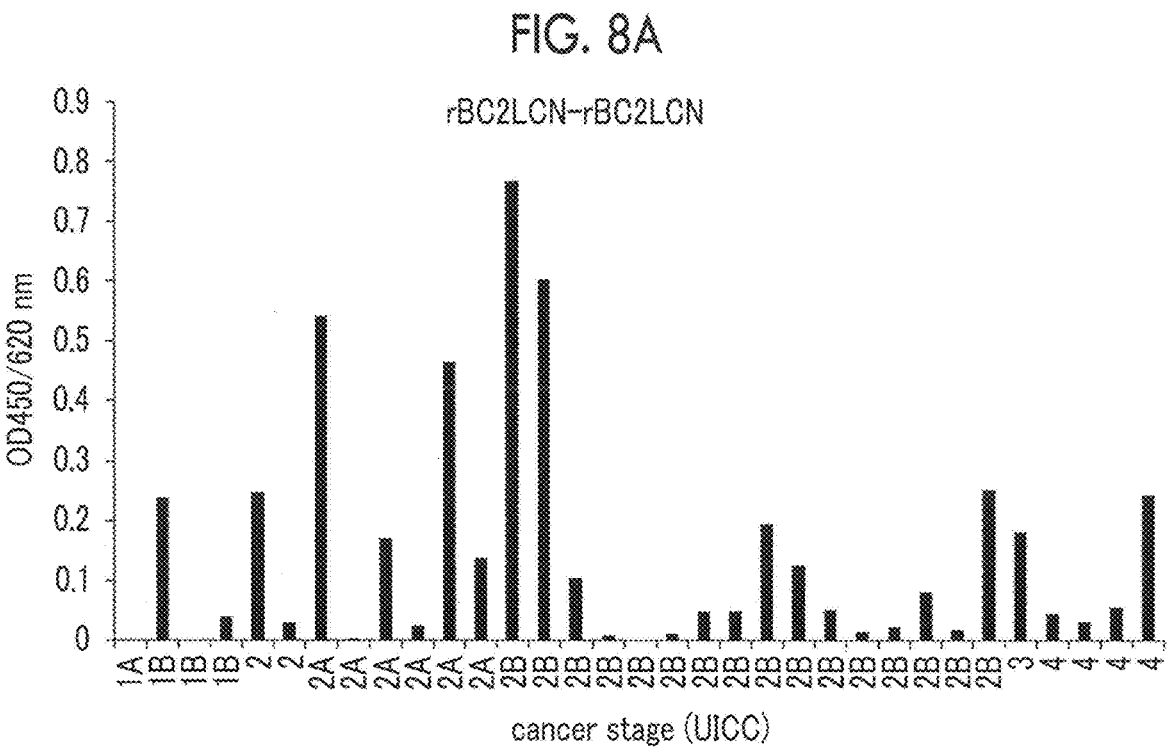

FIG. 8A shows the results of measuring a concentration of blood factors that can be simultaneously recognized by two molecules of BC2LCN in a blood sample of a pancreatic cancer patient for each stage in a UICC TMN classification.

Figure 8B:
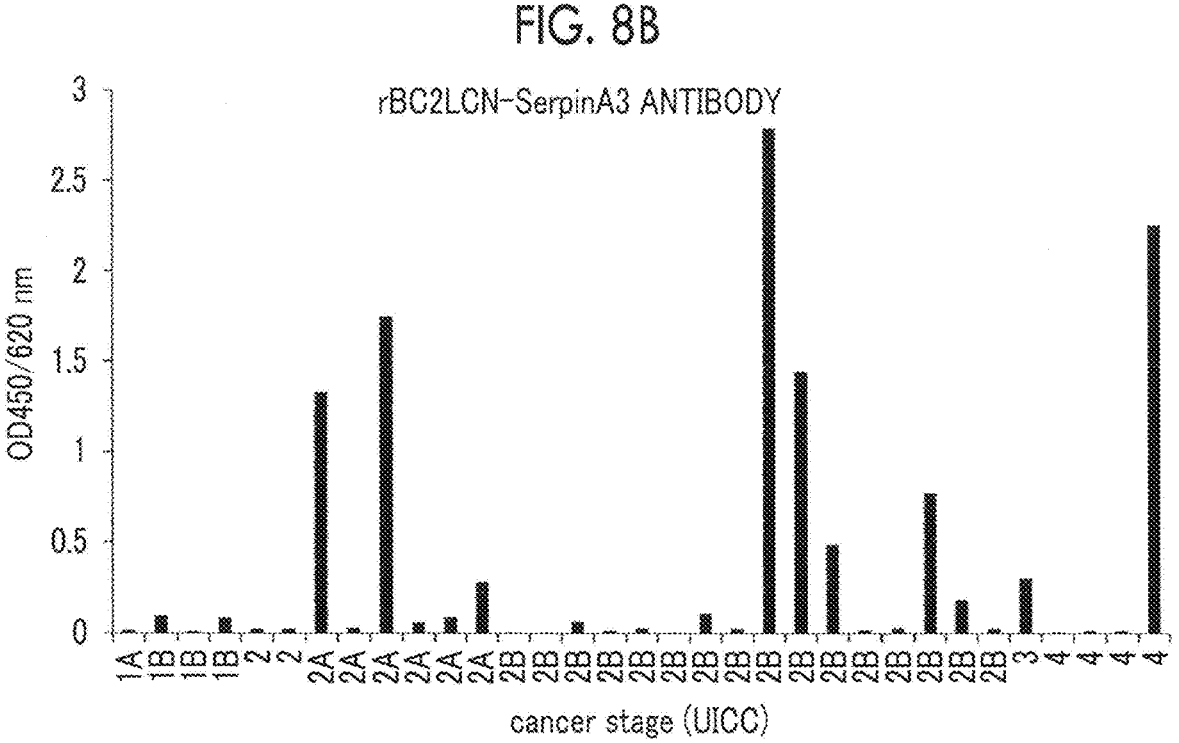

FIG. 8B shows the results of measuring a concentration of SerpinA3 bindable with BC2LCN in a blood sample of a pancreatic cancer patient for each stage in a UICC TMN classification.

Figures 8C, 8D:
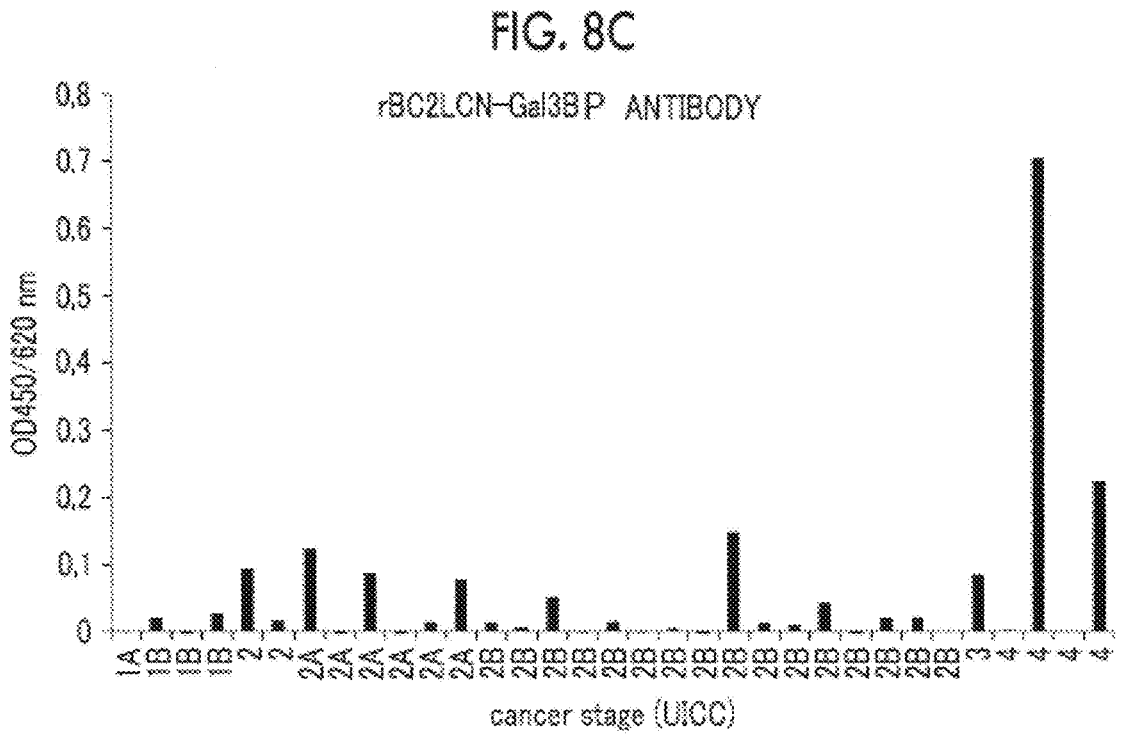

FIG. 8C shows the results of measuring a concentration of Gal3BP bindable with BC2LCN in a blood sample of a pancreatic cancer patient for each stage in a UICC TMN classification.

FIG. 8D shows the results of measuring a concentration of SerpinA3 in a blood sample of a pancreatic cancer patient measured using two different anti-SerpinA3 antibodies for each stage in a UICC TMN classification.

Figure 9:
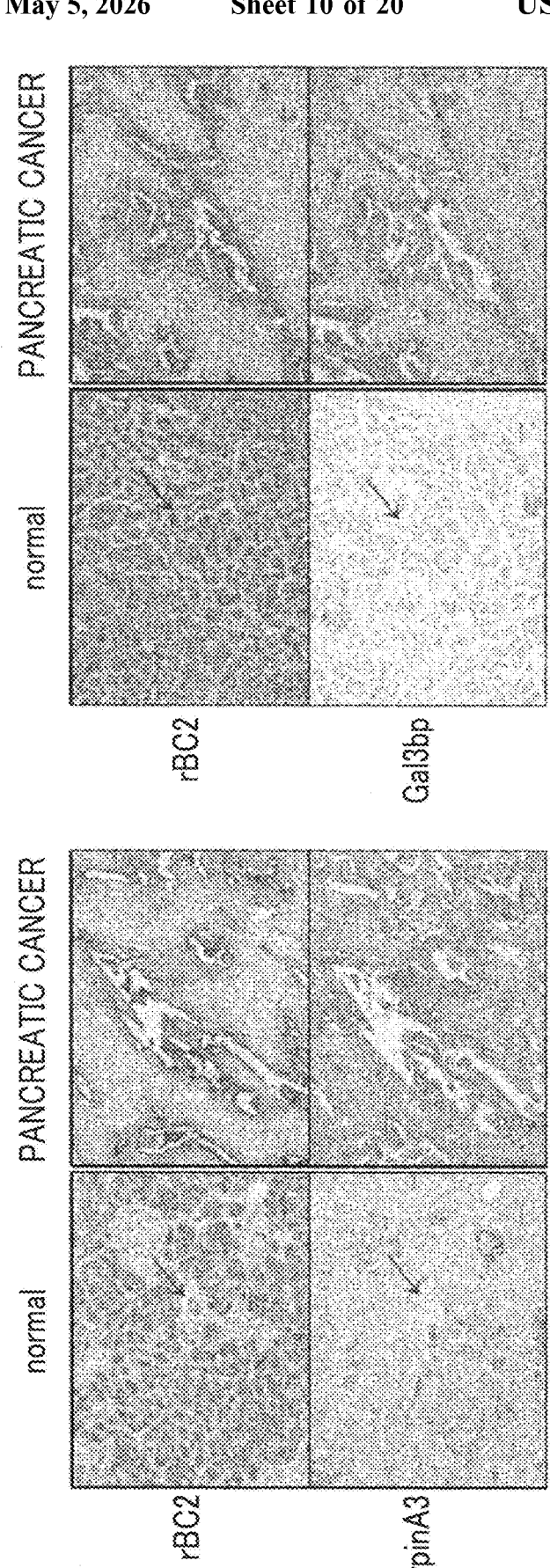

FIG. 9 shows the results of histological staining using rBC2LCN (sometimes simply referred to as "rBC2" in the drawings) of normal tissue sections and pancreatic tissue sections containing a pancreatic cancer, and immunohistological staining for SerpinA3 and Gal3BP.

Figure 10:
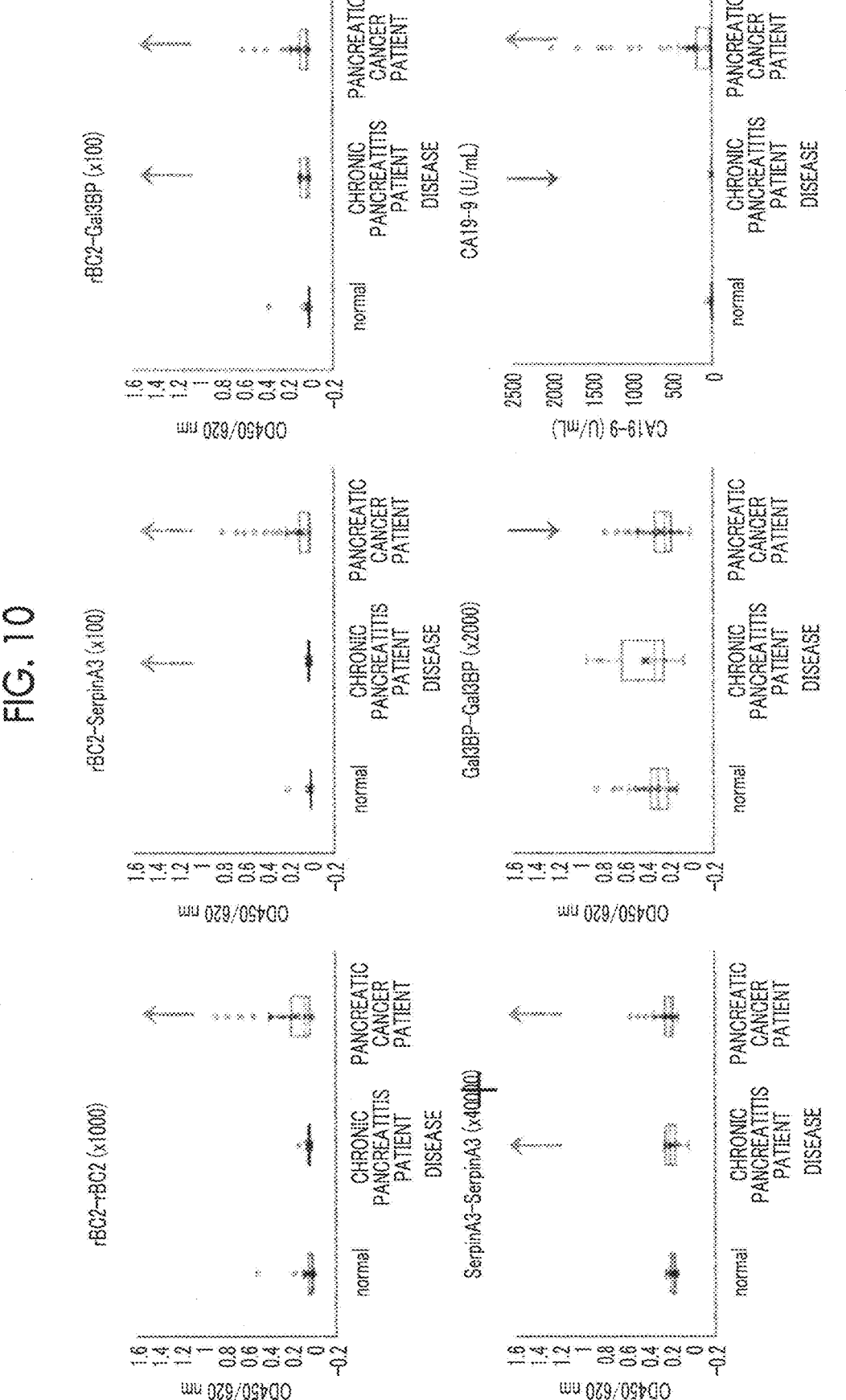

FIG. 10 shows the analysis results of blood samples of healthy persons, chronic pancreatitis patients, and pancreatic cancer patients in systems of a sandwich assay using two molecules of BC2LCN, a sandwich assay using BC2LCN and an anti-SerpinA3 antibody, a sandwich assay using BC2LCN and an anti-Gal3BP antibody, an ELISA using anti-SerpinA3 antibodies, and an ELISA using anti-Gal3BP antibodies.

FIG. 11 shows an ROC curve for detecting pancreatic cancer patients against healthy persons and chronic pancreatitis patients in systems of a sandwich assay using two molecules of BC2LCN, a sandwich assay using BC2LCN and an anti-SerpinA3 antibody, a sandwich assay using BC2LCN and an anti-Gal3BP antibody, an ELISA using anti-SerpinA3 antibodies, and an ELISA using anti-Gal3BP antibodies. The analysis was performed using blood samples.

Figure 12:
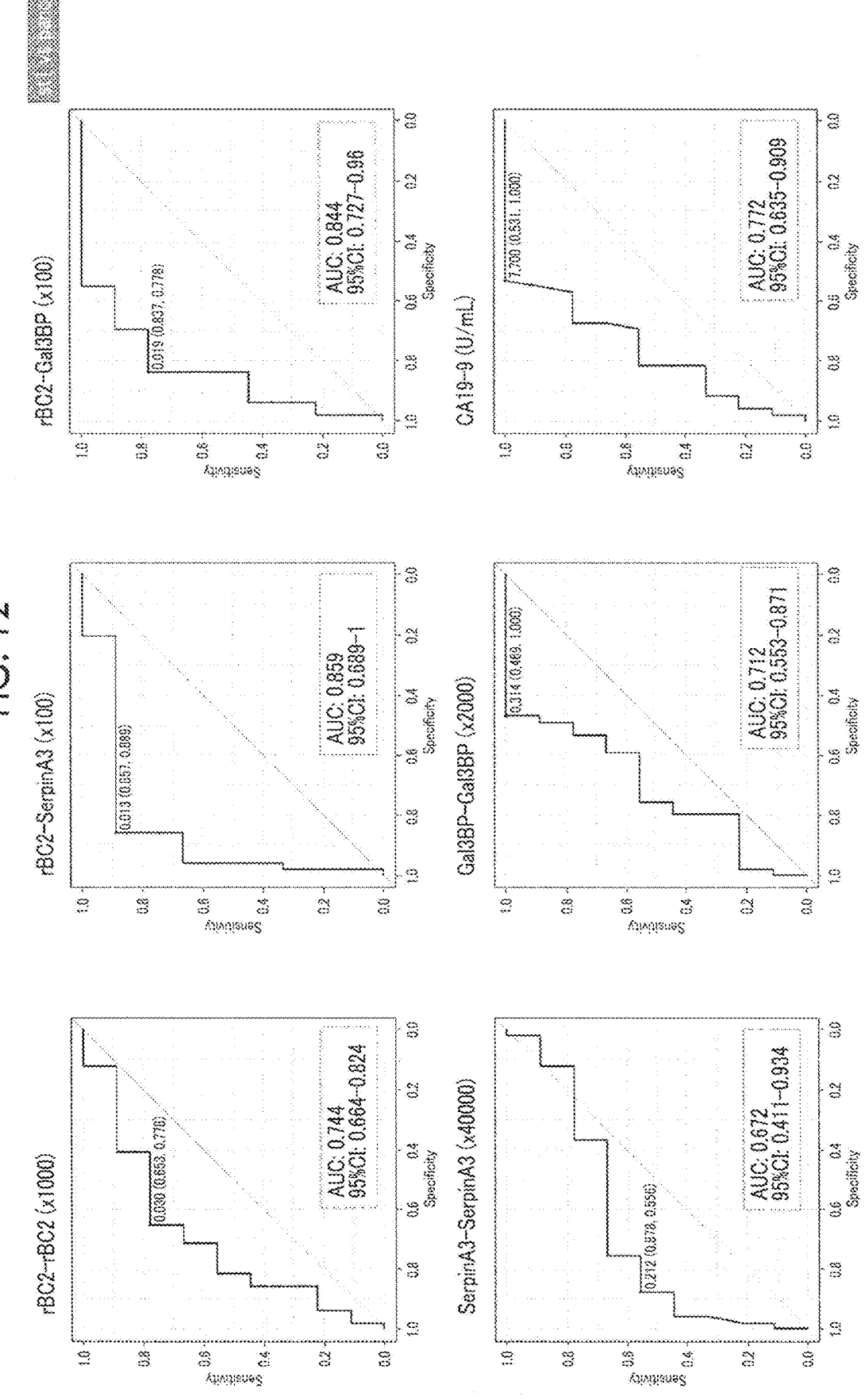

FIG. 12 shows an ROC curve for detecting stage I pancreatic cancer patients against healthy persons in systems of a sandwich assay using two molecules of BC2LCN, a sandwich assay using BC2LCN and an anti-SerpinA3 antibody, a sandwich assay using BC2LCN and an anti-Gal3BP antibody, an ELISA using anti-SerpinA3 antibodies, and an ELISA using anti-Gal3BP antibodies. The analysis was performed using blood samples.

Figure 13:
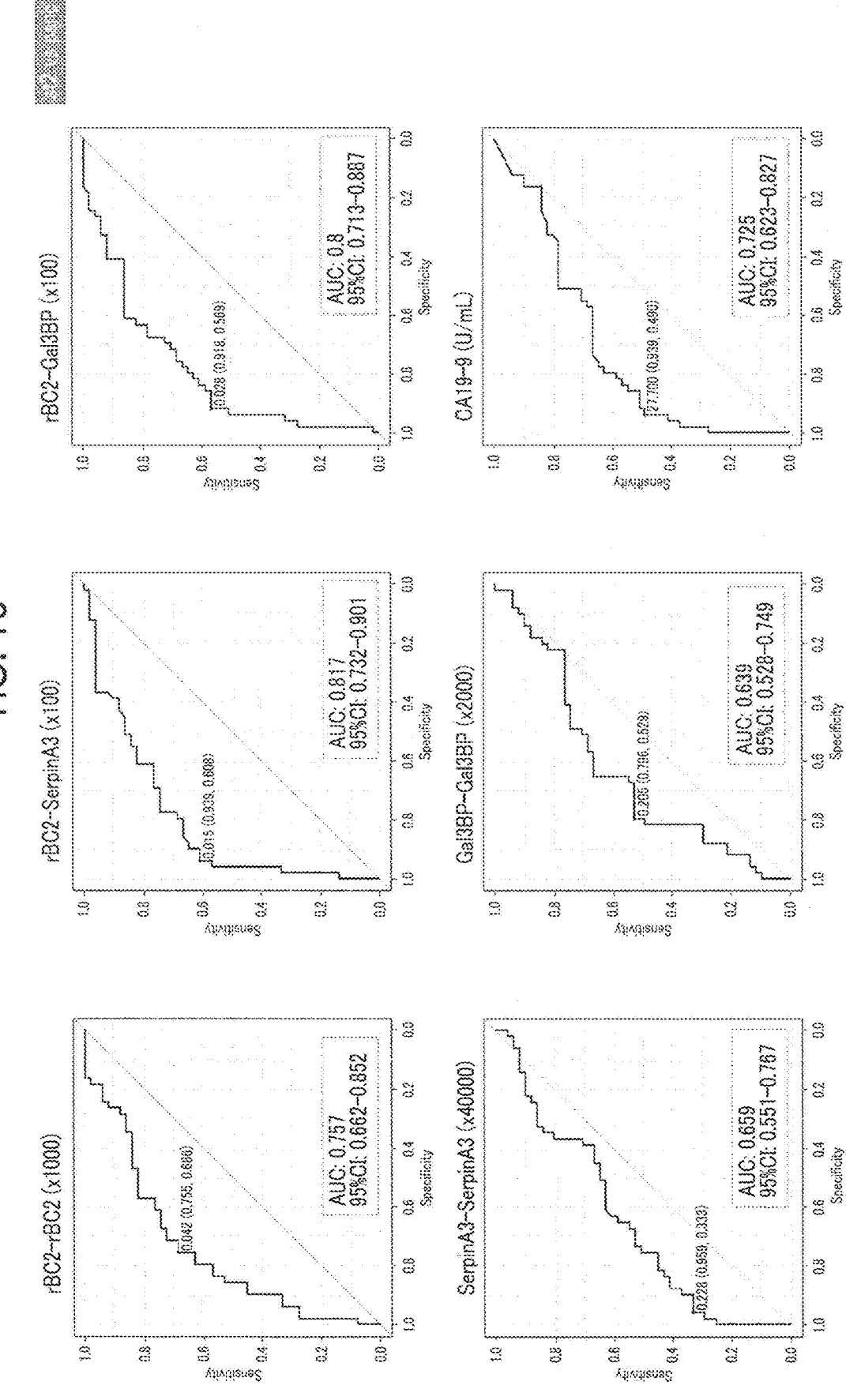

FIG. 13 shows an ROC curve for detecting stage II pancreatic cancer patients against healthy persons in systems of a sandwich assay using two molecules of BC2LCN, a sandwich assay using BC2LCN and an anti-SerpinA3 antibody, a sandwich assay using BC2LCN and an anti-Gal3BP antibody, an ELISA using anti-SerpinA3 antibodies, and an ELISA using anti-Gal3BP antibodies. The analysis was performed using blood samples.

Figure 14:
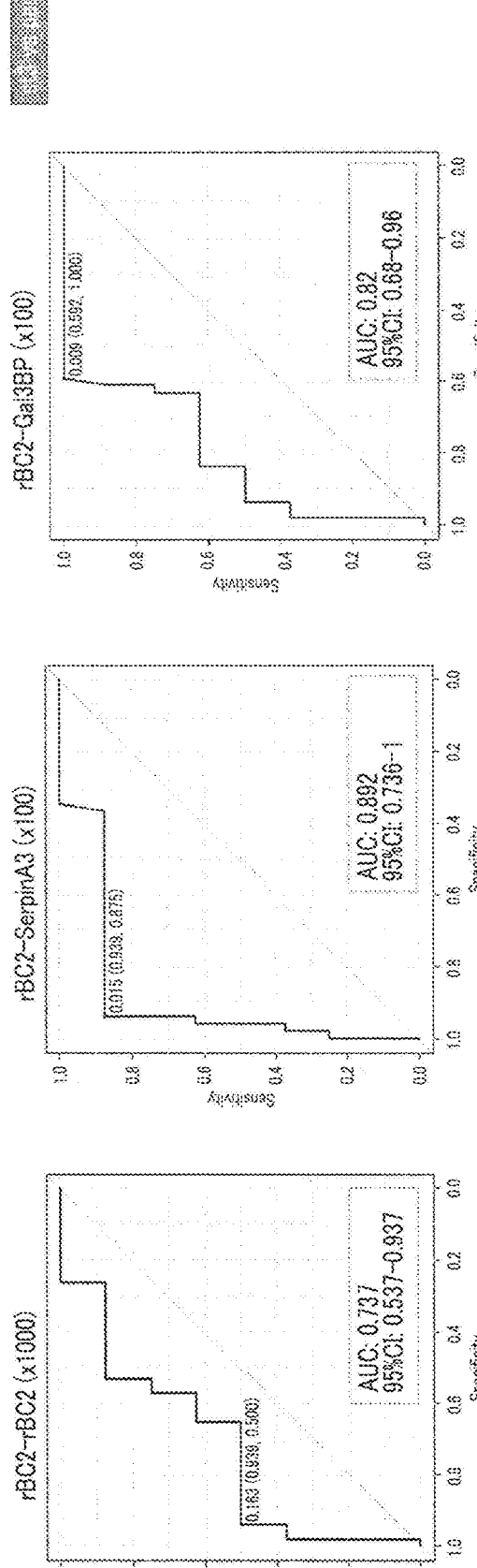

FIG. 14 shows an ROC curve for detecting stage III pancreatic cancer patients against healthy persons in systems of a sandwich assay using two molecules of BC2LCN, a sandwich assay using BC2LCN and an anti-SerpinA3 antibody, and a sandwich assay using BC2LCN and an anti-Gal3BP antibody. The analysis was performed using blood samples.

Figure 15:
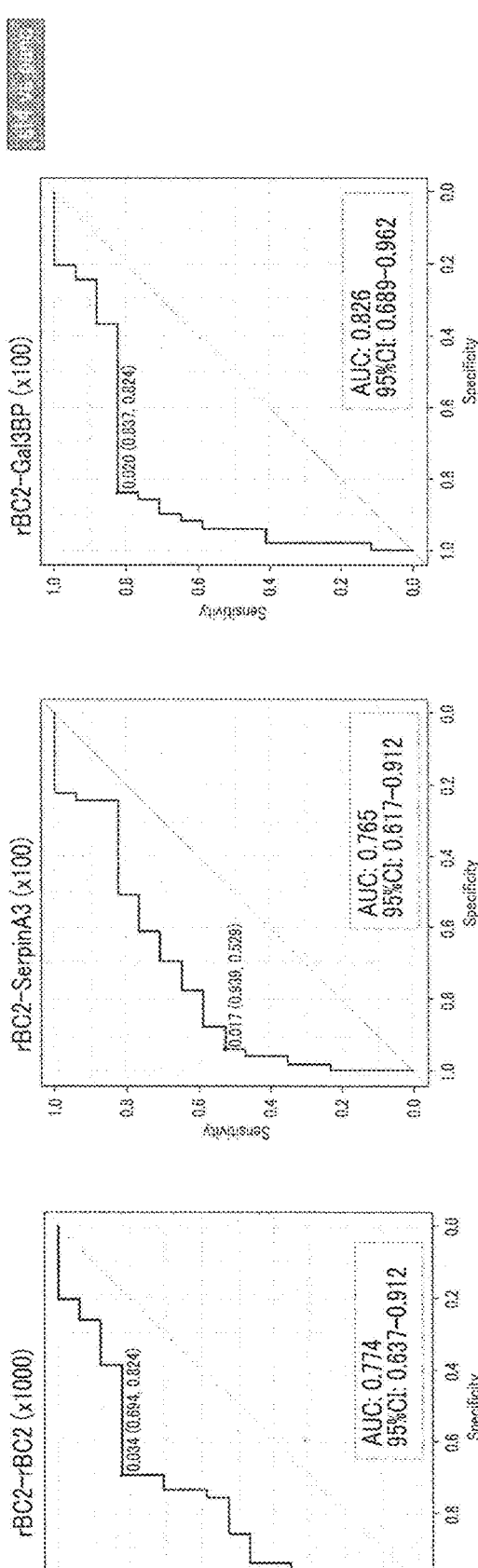

FIG. 15 shows an ROC curve for detecting stage IV pancreatic cancer patients against healthy persons in systems of a sandwich assay using two molecules of BC2LCN, a sandwich assay using BC2LCN and an anti-SerpinA3 antibody, and a sandwich assay using BC2LCN and an anti-Gal3BP antibody. The analysis was performed using blood samples.

Figure 16:
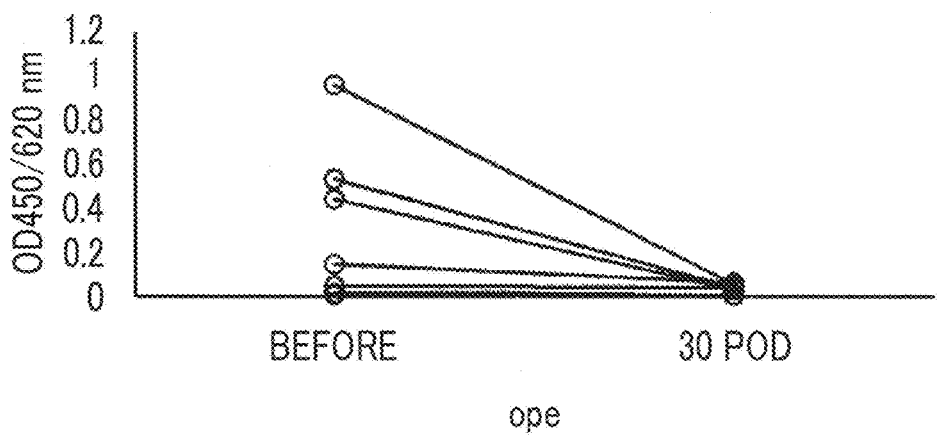
Figure 16:
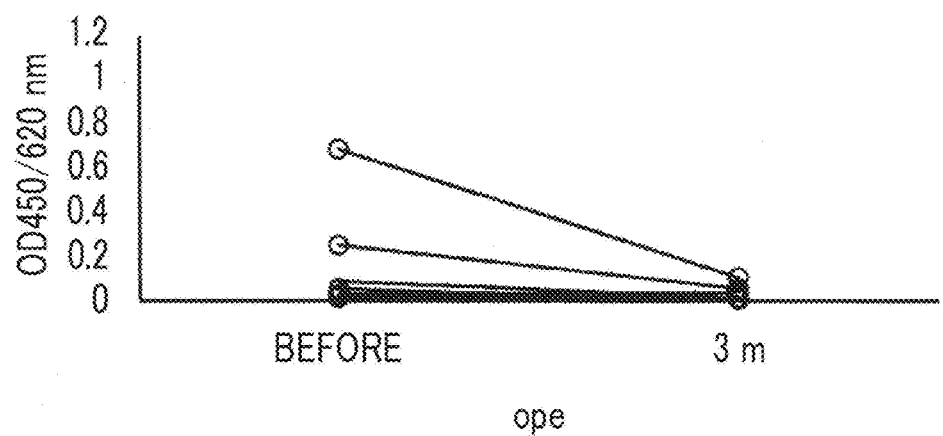

FIG. 16 shows the results of analyzing blood samples of patients before an operation to remove a pancreatic cancer, at 30 days after the operation (30 POD), and at 3 months after the operation (3 m) by a sandwich assay using BC2LCN and an anti-SerpinA3 antibody.

Figure 17:
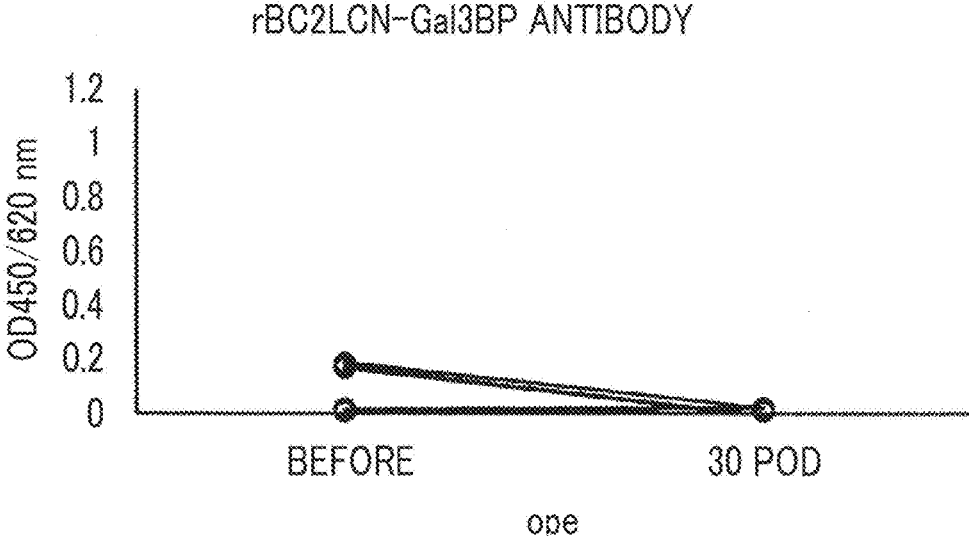
Figure 17:
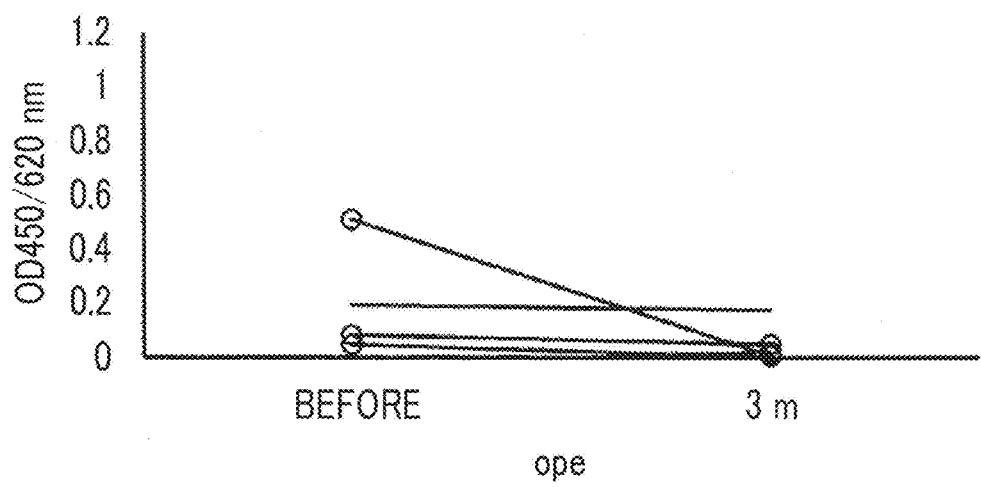

FIG. 17 shows the results of analyzing blood samples of patients before an operation to remove a pancreatic cancer, at 30 days after the operation (30 POD), and at 3 months after the operation (3 m) by a sandwich assay using BC2LCN and an anti-Gal3BP antibody.

Figure 18:
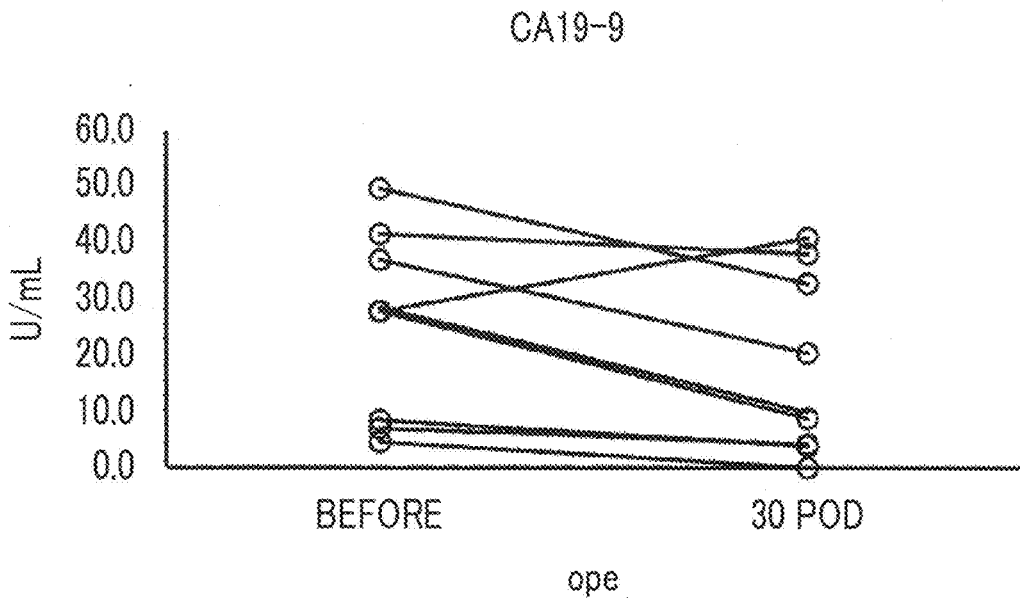
Figure 18:
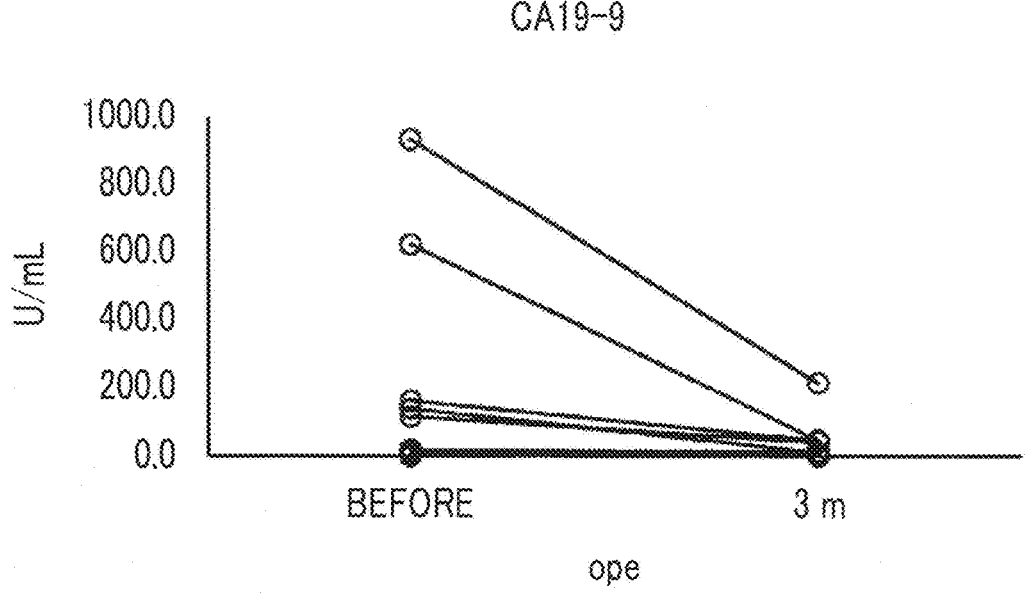

FIG. 18 shows the results of analyzing blood samples of patients before an operation to remove a pancreatic cancer, at 30 days after the operation (30 POD), and at 3 months after the operation (3 m) by ELISA using CA19-9.

Figure 19:
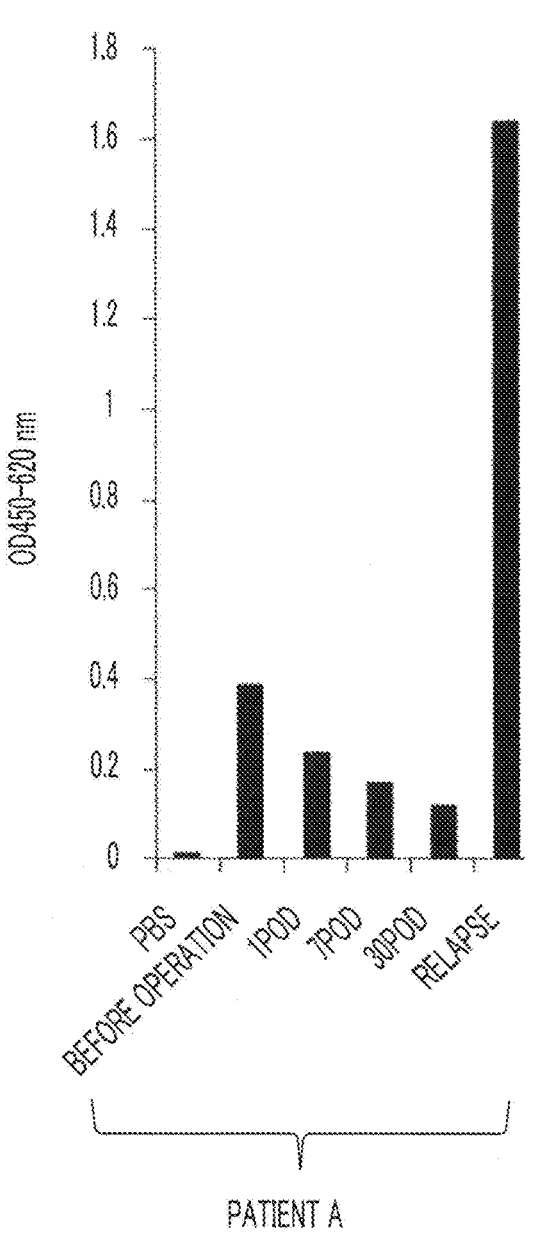

FIG. 19 shows the results of analyzing blood samples of a patient (patient A) before an operation to remove a pancreatic cancer, at 1 day after the operation (1 POD), at 7 days after the operation (7 POD), at 30 days after the operation (30 POD), and after relapse by a sandwich assay using BC2LCN and an anti-SerpinA3 antibody.

DESCRIPTION OF EMBODIMENTS

As used herein, a "subject" means a mammalian animal, in particular, mammals containing humans. As used herein, the "subject" can be a healthy person, or a patient having a cancer or a patient having a potential to have the cancer.

As used herein, a "tumor" means a cell population that exhibits self-sustaining proliferation. The self-sustaining proliferation means a property of cells that escape a normal cell proliferation control in the body and continue to proliferate autonomously. The tumors are roughly classified into benign tumors and malignant tumors (cancers). The benign tumors are tumors that proliferate self-sustainably but do not metastasize, infiltrate, or cause cachexia. The malignant tumors cause one or more of infiltration into normal tissue, metastasis, and cachexia, in addition to autonomous proliferation.

As used herein, a "biological sample" means a sample obtained from a subject (for example, tissues, cells, extracellular fluids, and body fluids). The body fluids contain blood, urine, ascites, pleural effusion, and secretions (for example, endocrine and exocrine fluids, such as digestive juices such as a pancreatic juice). As used herein, a "blood sample" is a blood obtained from a subject (for example, a peripheral blood) or a sample derived from the blood (for example, a serum and a plasma). As used herein, a "blood component" is a component contained in a blood, particularly a liquid component contained in the blood. In the present specification, in a case where a biological sample is a blood sample, the component is a blood component, as described later.

As used herein, an "antibody" means an immunoglobulin. The antibody is a biomolecule that has a property of binding to an antigen. The antibody can have specificity for an antigen. The antibody may be a monoclonal antibody or a polyclonal antibody. The antibody may contain a bispecific antibody. The antibody can be a full-length antibody and a fragment thereof having a property of binding to an antigen.

As used herein, "BC2LCN" is the N-terminal domain of BC2L-C which is a lectin derived from *Burkholderia cenocepacia* (Sulak, O., et al., Structure, 18(1): 59-72, 2010).

According to previous reports, it has been revealed that BC2LCN has affinity for glycoprotein sugar chains H-type 1 (Fucα1-2Galβ1-3GlcNAc) and H-type 3 (Fucα1-2Galβ1-3GalNAc), and it has also been revealed that BC2LCN can be used as an undifferentiated marker of human ES cells or iPS cells expressing a podocalyxin having an H-type 3 sugar chain (WO2014/126146). In addition, according to previous reports, it has been revealed that BC2LCN is specifically expressed in cancer tissues and can be used to detect a cancer (WO2017/061449A). According to WO2017/061449A, it has been confirmed that a sandwich assay of BC2LCN and an antibody binding to keratan sulfate confirms the presence of a protein recognized by BC2LCN and keratan sulfate in blood components of some cancer patients. As used herein, BC2LCN produced using a host other than *B. cenocepacia* such as *Escherichia coli* and the like may be referred to as a recombinant BC2LCN or rBC2LCN. As used herein, a sugar chain or protein to which BC2LCN binds is referred to as a sugar chain or protein bindable with BC2LCN. The protein bindable with BC2LCN is modified with a sugar chain bindable with BC2LCN. The sugar chain bindable with BC2LCN can be an H-type 1 sugar chain and/or an H-type 3 sugar chain. Examples of BC2LCN include a lectin registered as YP_002232818 at the National Center for Biotechnology Information (NCBI). As BC2LCN, any of those having a binding ability to a sugar chain can be used, but as BC2LCN, those having a modified binding ability to a sugar chain (for example, an improved ability to a sugar chain) as disclosed in JP2020-146027A can also be used. A variant of BC2LCN may be used. Examples of BC2LCN include a protein (BC2LCN) having an amino acid sequence of 90% or more, 95% or more, 96% or more, 97% or more, 98% or more, 99% or more or 100% identical to the amino acid sequence of a lectin registered as YP_002232818. BC2LCN binds to at least one or more selected from the group consisting of an H-type 3 sugar chain and an H-type 1 sugar chain.

As used herein, "SerpinA3" is a serine protease inhibitor (serpin) also known as an al antichymotrypsin (AACT). In humans, SerpinA3 can be, for example, a protein obtained by translation from an mRNA having a base sequence registered as GenBank registration number K01500.1. In humans, the SerpinA3 protein can be produced by cleavage of a 423 amino acid long precursor (for example, NCBI reference number: NP 001076.2) with a signal peptide consisting of the $1^{st}$ to $23^{rd}$ amino acid sequences.

As used herein, "Gal3BP" is a galectin-3-binding protein. Gal3BP can be a protein obtained by translation from an mRNA having a base sequence registered with the National Center for Biotechnology Information (NCBI) reference number NM 005567.4. In humans, the Gal3BP protein can be produced, for example, by cleavage from a 585 amino acid long precursor (for example, the precursor having an amino acid sequence registered as NCBI reference number: NP_005558.1) with a signal peptide consisting of the $1^{st}$ to $18^{th}$ amino acid sequences. Gal3BP has a molecular weight of 90 kDa in the serum and is found at a high concentration in the serum of patients with a breast cancer, a lung cancer, a rectal colorectal cancer, an ovarian cancer, and an endometrial cancer (Koths, K. et al., J. Biol. Chem. 268: 14245-14249, 1993).

As used herein, a "sandwich assay" is an assay used to detect a target component in a sample. The sandwich assay can be carried out by a person skilled in the art by an ordinary method. The sandwich assay is typically an assay in which a target component is brought into contact with a capturing molecule A binding to the target component immobilized on a support (for example, a substrate and beads) to capture the target component on the support, and the unbound target component removed (separated) and then brought into contact with a capturing molecule B binding to the labeled target component to detect the label of the target component captured on the support as an indicator. As the support that can be used in the present invention, any of supports (in particular, insoluble supports) used in ordinary immunological measurement methods can be used, but examples of the support include organic substances such as polystyrene, polyacrylic acid, polymethacrylic acid, polymethyl methacrylate, polyacrylamide, polyglycidyl methacrylate, polypropylene, polyolefin, polyimide, polyurethane, polyester, polyvinyl chloride, polyethylene, polychlorocarbonate, a silicone resin, silicone rubber, agarose, dextran, and an ethylene-maleic acid anhydride copolymerized substances; inorganic substances such as glass, silicon oxide, silica, porous glass, frosted glass, alumina, silica gel, and metal oxides; magnetic substances such as iron, cobalt, nickel, magnetite, and chromate; and those prepared using alloys in a case where these magnetic substances as a material. The immobilization can be performed on a solid phase (for example, surfaces of any of beads, magnetic beads, membranes, plates, and the like). Various commercially available ones can be used as the magnetic beads. As the magnetic beads, for example, the beads disclosed in WO2012/173002A may be used. In the sandwich assay, it is usually required that the capturing molecule A to be immobilized and the capturing molecule B labeled do not compete with each other for binding to a target component, and simultaneously bind to the target component. The capturing molecule A and the capturing molecule B can be a first molecule and a second molecule, each of which will be described later. The capturing molecule A and the capturing molecule B can be the second molecule and the first molecule, each of which will be described later.

The sandwich assay can also be performed with a microfluidic chip (micro-total analysis systems; μTAS). The microfluidic chip contains a flow passage, the flow passage has a sample introduction port, and for example, in a case where in the sample introduction port, a capturing molecule X having a polycation or a polyanion (for example, DNA) bound thereto is brought into contact with a sample to form a composite of the capturing molecule X and a target component, the composite is moved by application of an electric field and brought into contact with a labeled capturing molecule Y present in the middle of the flow passage to form a composite of the target component, the capturing molecule X, and the capturing molecule Y, and the composite is further moved in the flow passage by an electric field, thus reaching a detection unit on the flow passage, whereby detection can be performed by a label bound to the capturing molecule Y. The detection can be optically carried out, for example, by a laser or the like. The capturing molecule X and the capturing molecule Y can be the first molecule and the second molecule, respectively, each of which will be described later. The capturing molecule X and the capturing molecule Y can be the second molecule and the first molecule, respectively, each of which will be described later. The presence of a plurality of biomarkers can also be detected in parallel using μTAS.

Other examples of the sandwich assay include an assay (for example, AlphaLISA) in which in a case where a target molecule is present with a capturing molecule N and a capturing molecule M being each immobilized on different beads A and B, the target molecule forms a composite with the capturing molecule N and the beads A, and the capturing molecule M and the beads B form a composite, and only upon forming the composite (in a case where the beads A and B are in close proximity) by irradiating the beads A containing a photosensitizer releasing a single-term oxygen with excitation light, the single-term oxygen reaches the beads B, resulting in chemiluminescence of the beads B, and thus, the presence of a target molecule is detected by detecting the light from the beads B. Accordingly, the present invention may provide an AlphaLISA assay kit containing beads on which BC2LCN is immobilized and beads on which an antibody binding to SerpinA3 or Gal3BP is immobilized. In the present invention, an assay kit for detecting the presence of a target molecule, using fluorescence resonance energy transfer (FRET), bioluminescence resonance energy transfer (BRET), or the like between BC2LCN labeled with a first fluorescent molecule and an antibody binding to SerpinA3 or Gal3BP labeled with a second fluorescent molecule can also be used. In this case, beads or supports for Immobilization are not required. In the present invention, such a kit for an assay can be provided.

As used herein, an "immunochromatographic assay" is an assay used to detect a target component contained in a sample, and is usually an assay in which a capturing molecule C labeled with a label such as a gold colloid and a target component contained in a liquid sample are brought into contact with each other to form a composite of the labeled capturing molecule C and the target component, the composite is moved onto a chromatomembrane and brought into contact with a capturing molecule D immobilized on a test line to form a composite of the labeled capturing molecule C and the target component in the test line, whereby a label in the test line is detected as an indicator. In the immunochromatographic assay, it is usually required that the labeled capturing molecule C and the capturing molecule D immobilized in the test line do not compete with each other for binding to the target component, and need to simultaneously bind to the target component. In the immunochromatographic assay, a control line is provided in addition to the test line, and in the control line, a molecule binding to the capturing molecule C (in which the molecule is an antibody or the like, and in a case where the capturing molecule C is an IgG antibody, it can be an anti-IgG antibody) is immobilized, and thus, the labeled capturing component C which has not been bound to the target component can be captured. In the immunochromatographic assay, a strip containing a sample pad containing a sample, a conjugate pad in which the labeled capturing molecule C is present, a membrane as a moving layer in which a composite of the target component and the capturing molecule C in the sample moves, and an absorption pad which absorbs moisture in the sample are provided in this order is provided, and a test line in which the capturing molecule D is immobilized and a control line in which an antibody against the capturing molecule C is immobilized are present on the membrane. In a case where the sample is contained in the sample pad and the sample contains the target component, it moves on the strip toward the absorption pad. Upon moving to the conjugate pad, the labeled capturing molecule C and the target component form a composite, and the composite is captured by the capturing molecule D immobilized in the test line and also captured by the control line. In a case where the sample does not contain the target component, the sample moves towards the absorption pad and the labeled capturing molecule C does not form a composite, and thus, it is not captured in the test line, but is captured only in the control line. As a result, in a case where the control line develops color and the test line develops color, it is shown that the sample contains the target component, and in a case where the control line develops color and the test line does not develop color, it is shown that the sample does not contain the target component. In a case where the control line does not develop color, it can be determined that an evaluation system by the immunochromatography does not work properly. The capturing molecule C and the capturing molecule D can be the first molecule and the second molecule, respectively, each of which will be described later. The capturing molecule C and the capturing molecule D can be the second molecule and the first molecule, respectively, each of which will be described later.

As used herein, "lectin electrophoresis" is electrophoresis using a gel containing a lectin, and is a method for separating lectin-binding molecules by utilizing a fact that a molecule interacting with a lectin during electrophoresis has a lower moving speed than a molecule not interacting with the lectin. The lectin is liberate in a gel or immobilized on the gel. Since the lectin hardly moves by electrophoresis, the migration speed of a glycoprotein can be reduced by simply mixing with a gel material to create a gel. Alternatively, the lectin is non-covalently or covalently linked to the gel. In a case where the molecule bindable with BC2LCN is separated from the molecule non-bindable with BC2LCN, a biological sample can be separated by lectin electrophoresis using BC2LCN as the lectin. Since a molecule having a sugar chain bindable with BC2LCN repeatedly interacts with a lectin immobilized on a gel during migration, the migration is delayed. On the other hand, the non-molecule bindable with BC2LCN does not interact with a lectin immobilized on a gel, and the migration is fast. Using this principle, the molecule having a sugar chain bindable with BC2LCN and the molecule non-bindable with BC2LCN can be separated by electrophoresis. The lectin electrophoresis can be appropriately carried out by a person skilled in the art.

As used herein, "lectin affinity chromatography" is chromatography utilizing a fact that a lectin has a property of specifically binding to a sugar chain. In the lectin affinity chromatography, for example, affinity chromatography is performed on a sample, using a column containing an insoluble support on which a lectin is immobilized. In a case where a component in the sample has an affinity for a lectin, the component will be separated from the other components. In the present invention, for example, BC2LCN can be used as the lectin.

According to the present invention, analysis of the sera of patients with various cancers revealed that in a sandwich assay using immobilized BC2LCN and labeled BC2LCN, it was found that a blood component that can simultaneously bind to two BC2LCN's are present and an amount of the blood component in the serum of a patient with a cancer tends to be higher than that in a healthy person.

According to the present invention, further analysis of the sera of patients with various cancers revealed that in a sandwich assay using BC2LCN and an antibody binding to SerpinA3, it was found that SerpinA3 bindable with BC2LCN is present as a blood component and an amount of SerpinA3 bindable with BC2LCN in the serum of a patient with a cancer tends to be higher than that in a healthy persons.

According to the present invention, further analysis of the sera of patients with various cancers revealed that in a sandwich assay using BC2LCN and an antibody binding to Gal3BP, it was found that Gal3BP bindable with BC2LCN is present as a blood component and an amount of Gal3BP bindable with BC2LCN in the serum of a patient with a cancer tends to be higher than that in a healthy persons.

According to the present invention, there is provided a method for analyzing a biological
sample obtained from a subject, in which the method contains detecting one or more
components (sometimes referred to as a "target com-
ponent") selected from the group consisting of Ser-
pinA3 (for example, SerpinA3 bindable with
BC2LCN) and Gal3BP (for example, Gal3BP bindable
with BC2LCN) in the biological sample obtained from
the subject. The method of an embodiment of the
present invention may contain preparing the biological
sample. The method of the embodiment of the present
invention may further contain measuring an amount of
the components.

According to the present invention, one or more compo-
nents selected from the group consisting of SerpinA3 (for
example, SerpinA3 bindable with BC2LCN) and Gal3BP
(for example, Gal3BP bindable with BC2LCN) can be
detected using a molecule binding to the components.

In some aspects, the one or more components can be
detected after separating the one or more components from
the other components.

For example, SerpinA3 can be detected using a molecule
binding to SerpinA3. Two different molecules that can
simultaneously bind to SerpinA3 can also be used. SerpinA3
can be detected by an immunochromatographic assay or a
sandwich assay, using the two different molecules that can
simultaneously bind to SerpinA3. SerpinA3 can also be
detected by mass spectrometry. In either case, a calibration
curve can be obtained using a reference material of Ser-
pinA3. In addition, SerpinA3 can be quantified by applying
a measured value for SerpinA3 to a calibration curve thus
obtained.

In addition, SerpinA3 bindable with BC2LCN can be
detected using a molecule binding to a sugar chain bindable
with BC2LCN and a molecule binding to SerpinA3. For the
molecule binding to a sugar chain bindable with BC2LCN,
the detection may contain separating the molecule bindable
with BC2LCN from the others, using the molecule binding
to a sugar chain bindable with BC2LCN, and in a case where
the molecule binding to a sugar chain is BC2LCN, the
detection may contain separating the molecule bindable with
BC2LCN from the others, using lectin affinity chromatog-
raphy or lectin electrophoresis. In addition, the detection
may also contain separating SerpinA3 from the other com-
ponents. Either of the separation of SerpinA3 and the
separation of the component bindable with BC2LCN may be
carried out first.

For example, Gal3BP can be detected using a molecule
binding to Gal3BP. Two different molecules that can simul-
taneously bind to Gal3BP can also be used. Gal3BP can be
detected by an immunochromatographic assay or a sandwich
assay, using the two different molecules that can simultane-
ously bind to Gal3BP. Gal3BP can also be detected by mass
spectrometry. In either case, a calibration curve can be
obtained using a reference material of Gal3BP. In addition,
Gal3BP can be quantified by applying a measured value for
Gal3BP to a calibration curve thus obtained.

In addition, Gal3BP bindable with BC2LCN can be
detected using a molecule binding to a sugar chain bindable
with BC2LCN and a molecule binding to Gal3BP. For the
molecule binding to a sugar chain bindable with BC2LCN,
the detection may contain separating the molecule bindable
with BC2LCN from the others by using the molecule
binding to a sugar chain bindable with BC2LCN, and in a
case where the molecule binding to the sugar chain is
BC2LCN, the detection may contain separating the molecule bindable with BC2LCN from the others by using lectin
electrophoresis. In addition, the detection may also contain
separating Gal3BP from the other components. Either of the
separation of Gal3BP and the separation of the component
bindable with BC2LCN may be carried out first.

According to the present invention, there is provided a method for analyzing a biological
sample obtained from a subject, in which the method contains analyzing components
(sometimes referred to as a "target component") con-
tained in a biological sample by an assay using a first
molecule selected from the group consisting of a mol-
ecule binding to a sugar chain bindable with BC2LCN,
a molecule binding to SerpinA3, and a molecule bind-
ing to Gal3BP, and a second molecule that is BC2LCN.

The biological sample is a biological sample obtained
from the subject. The subject can be a subject who has a
cancer or has a potential to have the cancer. The cancer can
be, for example, a pancreatic cancer. The pancreatic cancer
can be, for example, a pancreatic cancer at a stage selected
from the group consisting of stages I, II, III, and IV, and can
be, for example, a stage I pancreatic cancer or a stage II
pancreatic cancer. Examples of the biological sample
include tissues, cells, and body fluids. The body fluids
contain a blood (for example, a plasma and a serum), sweat,
saliva, urine, ascites, pleural effusion, and secretions (for
example, endocrine fluids and exocrine fluids, for example,
digestive juices such as a pancreatic juice). The tissues and
the cells can be, for example, tissues and cells that are
cancers or are suspected to be cancers. Tissues and cells
contain, for example, portions that are cancers or are sus-
pected to be cancers.

Examples of the molecule binding to a sugar chain
bindable with BC2LCN include an antibody binding to a
sugar chain bindable with BC2LCN or a fragment bindable
with an antigen. Other examples of the molecule binding to
a sugar chain bindable with BC2LCN include an aptamer
binding to a sugar chain bindable with BC2LCN (for
example, a nucleic acid aptamer selected from the group
consisting of DNA and RNA). Still other examples of the
molecule binding to a sugar chain bindable with BC2LCN
include a middle-molecular material such as a cyclic pep-
tide. These molecules binding to a sugar chain bindable with
BC2LCN can be obtained by methods known to a person
skilled in the art. For example, the antibody binding to a
sugar chain bindable with BC2LCN can be obtained from a
non-human mammalian animal immunized with a sugar
chain bindable with BC2LCN. The aptamer binding to a
sugar chain bindable with BC2LCN can be obtained from a
nucleic acid pool by utilizing the affinity for a sugar chain
bindable with BC2LCN. The cyclic peptide binding to a
sugar chain bindable with BC2LCN can be obtained from a
cyclic peptide pool by utilizing the affinity for a sugar chain
bindable with BC2LCN. The molecule binding to a sugar
chain bindable with BC2LCN can be, for example,
BC2LCN.

Examples of the molecule binding to SerpinA3 include an
antibody binding to SerpinA3 or a fragment bindable with
an antigen. Other examples of the molecule binding to
SerpinA3 include an aptamer binding to SerpinA3 (for
example, a nucleic acid aptamer selected from the group
consisting of DNA and RNA). Still other examples of the
molecule binding to SerpinA3 include a middle-molecular
material such as a cyclic peptide. These molecules binding
to SerpinA3 can be obtained by methods known to a person
skilled in the art. For example, the antibody binding to
SerpinA3 can be obtained from a non-human mammalian animal immunized with SerpinA3. The aptamer binding to SerpinA3 can be obtained from a nucleic acid pool by utilizing the affinity for SerpinA3. The cyclic peptide binding to SerpinA3 can be obtained from a cyclic peptide pool by utilizing the affinity for SerpinA3. SerpinA3 may form a composite with other components in a biological specimen in some cases. In the present invention, such a composite may be detected. Examples of other components forming a composite with SerpinA3 include PSA. Therefore, SerpinA3 can also be detected using a molecule binding to PSA and a molecule binding to SerpinA3. Alternatively, labeled recombinant PSA can also be used to detect SerpinA3 by utilizing a binding property of SerpinA3 to PSA.

Examples of the molecule binding to Gal3BP include an antibody binding to Gal3BP or a fragment bindable with an antigen. Other examples of the molecule binding to Gal3BP include an aptamer binding to Gal3BP (for example, a nucleic acid aptamer selected from the group consisting of DNA and RNA). Still other examples of the molecule binding to Gal3BP include a middle-molecular material such as a cyclic peptide. These molecules binding to Gal3BP can be obtained by methods known to a person skilled in the art. For example, an antibody binding to Gal3BP can be obtained from a non-human mammalian animal immunized with Gal3BP. The aptamer binding to Gal3BP can be obtained from a nucleic acid pool by utilizing the affinity for Gal3BP. The cyclic peptide binding to Gal3BP can be obtained from a cyclic peptide pool by utilizing the affinity for Gal3BP. Gal3BP may form a composite with other components in a biological specimen in some cases. In the present invention, such a composite may be detected. Examples of other components forming a composite with Gal3BP include galectin (in particular, galectin 3). Therefore, Gal3BP can also be detected using a molecule binding to galectin (in particular, galectin 3) and a molecule binding to Gal3BP. Alternatively, Gal3BP can be detected using labeled recombinant galectin (in particular, galectin 3) by utilizing a binding property of Gal3BP to galectin (in particular, galectin 3).

According to the present invention, there is provided a method for analyzing a biological sample (for example, a blood sample) obtained from a subject, in which the method contains analyzing the presence or absence or the concentration of a component (a specific component, for example, a blood component) in a biological sample (for example, a blood sample), and the component (for example, the blood component) is a component (sometimes referred to as a target component (for example, a target blood component)) selected from the group consisting of a component that simultaneously binds two BC2LCN's, SerpinA3 (for example, SerpinA3 bindable with BC2LCN), and Gal3BP (for example, Gal3BP bindable with BC2LCN). In the analysis method of the embodiment of the present invention, in a case where one, two, or all of the components are detected, it is indicated that the subject can be a cancer. In the analysis method of the embodiment of the present invention, in a case where the concentration of one of the components is higher than the cut off value, it is indicated that the subject can be a cancer.

In the analysis method of the embodiment of the present invention, the subject can be a human, for example, a healthy person, a patient having a cancer, and a patient having a potential to have a cancer.

In some aspects, the cancer can be one or more cancers selected from the group consisting of a pancreatic cancer, a colorectal cancer, a rectal adenocarcinoma, a bladder cancer, a breast cancer, a non-small cell lung cancer, a gastric cancer, a cervical cancer, a uterine cancer, a hepatocellular carcinoma, a thyroid cancer, a prostate cancer, a melanoma, an esophageal cancer, an ovarian cancer, a bile duct cancer, a non-Hodgkin's lymphoma, and a chronic myeloid leukemia. In some aspects, the cancer can be the pancreatic cancer. In some aspects, the pancreatic cancer can be a pancreatic cancer at a stage selected from the group consisting of stages I and II. In some aspects, the pancreatic cancer can be at the stage I. In some aspects, the pancreatic cancer can be at the stage II.

In some aspects, the target component or the target blood component is a component that can simultaneously bind to two BC2LCN's. In some aspects, the target component or the target blood component is SerpinA3 bindable with BC2LCN. In some aspects, the target component or the target blood component is Gal3BP bindable with BC2LCN. In these aspects, the cancer can be as described above and can be one or more selected from the group consisting of, for example, a pancreatic cancer, a colorectal cancer, a rectal adenocarcinoma, a bladder cancer, a breast cancer, a uterine cancer, a hepatocellular carcinoma, a thyroid cancer, a melanoma, an esophageal cancer, a bile duct cancer, an ovarian cancer, a non-Hodgkin's lymphoma, and a chronic myeloid leukemia. In some aspects, the cancer can be the pancreatic cancer. In some aspects, the pancreatic cancer can be a pancreatic cancer at a stage selected from the group consisting of stages I and II. In some aspects, the pancreatic cancer can be at the stage I. In some aspects, the pancreatic cancer can be at the stage II.

In some aspects, the cut off value can be, for example, 0, or the first quartile value, the average value, the third quartile value, or the maximum value of concentrations of target components (for example, target blood components) of a group of healthy persons, or a value between any two of these values (for example, the third quartile value or the maximum value, or a value therebetween). In some aspects, the cut off value can be, for example, 0, or the first quartile value, the average value, the third quartile value, or the maximum value of concentrations of target components (for example, target blood components) of a group of cancer patients, or a value between any two of these values.

In some aspects, the cut off value can be a cut off value at a point nearest to a point with a sensitivity of 1 and a specificity of 1 on an ROC curve, a value greater than the cut off value, or a value smaller than the cut off value. In some aspects, the cut off value can also be a cut off value at a point such that the Youden index is a maximum value, a value greater than the cut off value, or a value smaller than the cut off value.

The cut off value can be determined by a balance between a sensitivity and a false positive rate. The cut off value can be set low in a case where it is intended to detect as many cancer patients as possible (in a case where it is intended to increase the sensitivity) even with high false positiveness, whereas the cut off value can be set high in a case where it is intended to reduce the false positiveness (alternatively, in a case where the sensitivity may be decreased), and thus, a person skilled in the art can set it appropriately according to the purpose of inspection.

In the analysis method of the embodiment of the present invention, it is possible to obtain information that a subject has a potential to have a cancer in a case where the concentration of a target component (for example, a target blood component) in a biological sample (for example, a blood sample) obtained from the subject is higher than a cut off value. Therefore, the analysis method of the embodiment of the present invention can contain providing information indicating that a subject has a potential to have a cancer in a case where the concentration of a target component (for example, a target blood component) in a biological sample (for example, blood sample) obtained from the subject is higher than a cut off value.

In the analysis method of the embodiment of the present invention, it is possible to obtain information that a subject may have a pancreatic cancer in a case where the concentration of a target component (for example, a target blood component) in a biological sample (for example, a blood sample) obtained from the subject is higher than a cut off value. Therefore, the analysis method of the embodiment of the present invention can contain providing information indicating that a subject may have a pancreatic cancer in a case where the concentration of a target component (for example, a target blood component) in a biological sample (for example, blood sample) obtained from the subject is higher than the cut off value.

In the analysis method of the embodiment of the present invention, a target component (for example, a target blood component) can be also detected in a biological sample (for example, a blood sample) of patients having early stage cancers (at stages I and II). Therefore, the analysis method of the embodiment of the present invention contains providing information indicating that a subject may have an early stage cancer in a case where the concentration of a target component (for example, a target blood component) in a biological sample (for example, a blood sample) obtained from the subject is higher than the cut off value. The early stage cancer can be an early stage pancreatic cancer. The stage classification of the pancreatic cancer can be determined by a doctor, based on a UICC TNM classification (UICC: TNM Classification of Malignant Tumors, 8th Edn. Wiley-Blackwell; 2017. 94-95). The stage I contains stages 1A and 1B, and the stage II contains stages IIA and IIB. The stages III and IV have the same definitions as the stages III and IV, respectively.

TABLE 1

| Stage classification of pancreatic cancers (UICC TMN, 8th Edn) | | | | |
|---|---|---|---|---|
| | Metastasis to regional lymph nodes | | | Metastasis |
| | | Occurrence | | to |
| | Not occurred | 1 to 3 | 4 or more | distant organs |
| The size of a pancreatic cancer is 2 cm or less | 1A | 2B | 3 | 4 |
| The size of a pancreatic cancer is more than 2 cm and 4 cm or less | 1B | | | |
| The size of a pancreatic cancer is more than 4 cm | 2A | | | |
| A cancer extends to the celiac artery, the superior mesenteric artery, or the common hepatic artery | | | 3 | |

The information can be provided by transmission or output of the information. The information can be output on a display or a printed matter.

The analysis method of the embodiment of the present invention may further contain determining that a subject has a potential to have a cancer.

According to the present invention, it is possible to provide a method for treating a cancer, containing subjecting at least a part of subjects determined to have a cancer by the analysis method of the embodiment of the present invention to a cancer therapy. Examples of the cancer therapy include one or more selected from the group consisting of radiation therapy, chemotherapy, and surgical therapy. The cancer therapy can be standard therapy. The radiation therapy can contain irradiating the cancer with radiation. The chemotherapy may contain administering an anticancer agent to a subject. The surgical therapy may contain removing a cancer. Examples of the chemotherapy for a cancer (for example, a pancreatic cancer) include folfirinox therapy, gemcitabine.nabpaclitaxel therapy (GnP therapy), gemcitabine.S1 therapy (GS therapy), liposomal irinotecan.5FU/ LV therapy (Nal-IRI/FL therapy), gemcitabine therapy, and S1 therapy, and the subject can be treated by any one or more of these therapies. Examples of the anticancer agent include one or more selected from the group consisting of platinum preparations such as oxaliplatin, irinotecan, liposome-type irinotecan, levofolinate, gemcitabine, nabpaclitaxel, 5-fluorouracil (5-FU), and S-1.

According to the present invention, it is possible to provide a pharmaceutical composition containing a therapeutically effective amount of one or more selected from the group consisting of the anticancer agents, in which the pharmaceutical composition is used to treat a cancer in a subject determined to have a potential to have a cancer in the analysis method of the embodiment of the present invention. The pharmaceutical composition may further contain a pharmaceutically acceptable excipient, in addition to the pharmaceutically active ingredient. The pharmaceutically acceptable excipient can be appropriately selected by a person skilled in the art.

In some aspects of the analysis method of the embodiment of the present invention, there is provided a method for analyzing a biological sample (for example, a blood sample) obtained from a subject, in which the method contains analyzing a component (for example, a blood component) contained in a biological sample (for example, a blood sample) by a sandwich assay or an immunochromatographic assay, using a first molecule selected from the group consisting of BC2LCN, an antibody binding to SerpinA3, and an antibody binding to Gal3BP, and a second molecule that is BC2LCN.

In some aspects, the first molecule is immobilized on a support (for example, a substrate) and the second molecule can be labeled. In some aspects, the first molecule can be labeled and the second molecule can be immobilized on the support.

For Immobilization, for example, a known Immobilization method such as a direct method, a polystyrene tag method (WO2018/190357), a biotin-streptavidin method, a HaloTag method, a method using a chemical bond such as an amine coupling method, and a V5 tag method can be used. In the direct method, a capturing molecule to be immobilized is directly brought into contact with a support to be immobilized on a support. In the polystyrene tag method, a polystyrene tag is immobilized on a polystyrene plate via the polystyrene tag fused to a capturing molecule. In the biotin-streptavidin method, a capturing molecule modified with biotin is bound to a support coated with streptavidin so that the capturing molecule is immobilized on the support. In the HaloTag method, a capturing molecule is immobilized on a support coated with HaloTag via a HaloTag protein fused to the capturing molecule. In the amine coupling method, a carboxy group formed on the surface of a solid phase can be active-esterified, and a protein or the like can be immobilized thereon by a chemical bond via an amino group. In the V5 tag method, a capturing molecule to which a V5 tag is linked is bound to a support coated with an anti-V5 tag antibody so that the capturing molecule is immobilized on the support.

As a label, a substrate (a chromogenic substrate, a fluorescent substrate, and a luminescent substrate) or an enzyme used in an enzyme-labeled antibody method (for example, a peroxidase, a glucose oxidase, and an alkaline phosphatase) can be used in a sandwich assay. The labeling can be performed by a person skilled in the art, using an ordinary method. The labeling can be performed, for example, by a covalent bonding property. The labeling may be performed, for example, by reacting a biotin-linked antibody with an avidin-linked label. Examples of the substrate include a fluorescent substrate. As the peroxidase, for example, a horseradish peroxidase can be used. The horseradish peroxidase produces luminescence, fluorescence, or chemiluminescence by adding a chromogenic substrate, a fluorescent substrate, or a luminescent substrate. Therefore, the presence of a capturing molecule labeled with luminescence, fluorescence, or chemiluminescence as an indicator can be detected. Examples of the chromogenic substrate for a horseradish peroxidase include tetramethylbenzidine (TMB), o-phenylenediamine (OPD), 2,2'-azinobis[3-ethyl-benzothiazoline-6-sulfonic acid (ABTS), and Amplex (trademark) Red, and the chromogenic substrate can be used to detect a labeled molecule in the presence of hydrogen peroxide. Examples of the luminescent substrate for an alkaline phosphatase include p-nitrophenyl phosphate (pNPP), 4-methylumbelliferyl phosphate (4-MUP), and AttoPhos (trademark), and the luminescent substrate can be used to detect a capturing molecule. The glucose oxidase oxidizes glucose to generate gluconic acid and hydrogen peroxide. Hydrogen peroxide can be easily detected, for example, by using a colorimetric probe for detecting hydrogen peroxide (for example, a peroxidase). Hydrogen peroxide can develop color, for example, in the presence of a peroxidase and a chromogenic substrate thereof.

As the label, a dye (for example, a coloring agent such as gold colloid) can be used in an immunochromatographic assay.

In some aspects, the first molecule is BC2LCN. In this aspect, recombinant BC2LCN can be used as BC2LCN. BC2LCN may be directly immobilized, or immobilized on, for example, a streptavidin (or neutravidin)-coated support which is biotin-labeled. Alternatively, BC2LCN may be fused with a HaloTag protein and then immobilized on a support coated with a HaloTag ligand. In addition, BC2LCN may be fused with a polystyrene tag and then directly immobilized on a polystyrene plate. In either of a sandwich assay and an immunochromatographic assay, in a case where the first molecule is BC2LCN, a target component binds simultaneously to both the first molecule BC2LCN and the second molecule BC2LCN. Therefore, the target component detected by the sandwich assay and the immunochromatographic assay in which the first molecule is BC2LCN is a component which can bind simultaneously to a plurality of BC2LCN's. In the immunochromatographic assay, an antibody against BC2LCN or a sugar chain antigen binding to BC2LCN such as an H-type 1 sugar chain antigen and an H-type 3 sugar chain antigen can be immobilized in the control line.

In some aspects, the first molecule is an antibody binding to SerpinA3. In this aspect, it is considered that SerpinA3 having a sugar chain bindable with BC2LCN has been detected. The antibody binding to SerpinA3 can be prepared by an ordinary method, using bindability to SerpinA3 as an indicator.

The antibody binding to SerpinA3 may be further confirmed to have bindability to SerpinA3 having a sugar chain bindable with BC2LCN. SerpinA3 having a sugar chain bindable with BC2LCN can be purified as a component that reacts with immobilized BC2LCN and an antibody binding to SerpinA3, as used in Examples. The antibody binding to SerpinA3 may be selected, based on whether or not it binds to the purified component.

In an aspect in which the first molecule is an antibody binding to SerpinA3, the first molecule can be immobilized on a support (for example, a substrate or beads), and the second molecule can be labeled; or the first molecule can be labeled and the second molecule can be immobilized on the support.

In some aspects, the first molecule is an antibody binding to Gal3BP. In this aspect, it is considered that Gal3BP having a sugar chain bindable with BC2LCN is detected. The antibody binding to Gal3BP can be prepared by an ordinary method, using bindability to Gal3BP as an indicator.

The antibody binding to Gal3BP may be further confirmed to have bindability to Gal3BP having a sugar chain bindable with BC2LCN. Gal3BP having a sugar chain bindable with BC2LCN can be purified as a component that reacts with immobilized BC2LCN and an antibody binding to Gal3BP, as used in Examples. The antibody binding to Gal3BP may be selected using whether or not it binds to the purified component as an indicator.

In an aspect in which the first molecule is an antibody binding to Gal3BP, the first molecule can be immobilized on a support (for example, a substrate or beads), and the second molecule can be labeled; or the first molecule can be labeled and the second molecule can be immobilized on the support.

According to the present invention, there is provided a method for predicting whether or not a subject is a cancer, a method for obtaining preliminary information on whether or not a subject is a cancer, a method for determining whether or not a subject is a cancer, a method or preliminary method for predicting whether or not a subject is a cancer, a method for detecting a cancer in a subject, a method for detecting a cancer cell in a subject, a method for detecting a biomarker for a cancer in a subject (in which the biomarker is a component selected from the group consisting of a component that can simultaneously bind to two BC2LCN's, SerpinA3 bindable with BC2LCN, and Gal3BP bindable with BC2LCN), or a method for analyzing whether or not a subject is a cancer, in which the method contains:

analyzing the presence or absence or the concentration of a component (for example, a blood component) in a biological sample (for example, a blood sample), and the component (for example, the blood component) is a component selected from the group consisting of a component that can simultaneously bind to two BC2LCN's, SerpinA3 bindable with BC2LCN, and Gal3BP bindable with BC2LCN; or analyzing a component (for example, a blood component) contained in a biological sample (for example, a blood sample) by a sandwich assay or an immunochromatographic assay, using a first molecule selected from the group consisting of BC2LCN, an antibody binding to SerpinA3, and an antibody binding to Gal3BP, and a second molecule that is BC2LCN.

According to the present invention, there is provided a method for detecting a component (for example, a blood component) in a biological sample (for example, a blood sample) of a subject, in which the component (for example, the blood component) is a component selected from the group consisting of a component that can simultaneously bind to two BC2LCN's, SerpinA3 bindable with BC2LCN, and Gal3BP bindable with BC2LCN. This method contains bringing a first molecule selected from the group consisting of BC2LCN, an antibody binding to SerpinA3, and an antibody binding to Gal3BP, and a second molecule that is BC2LCN into contact with a biological sample (for example, a blood sample), and as a result, detecting a composite of a component thus formed (for example, a blood component), the first molecule, and the second molecule. This method can contain detecting a component (for example, a blood component) by a sandwich assay or an immunochromatographic assay, using a first molecule selected from the group consisting of BC2LCN, an antibody binding to SerpinA3, and an antibody binding to Gal3BP, and a second molecule that is BC2LCN.

According to the present invention, there is provided a kit for a sandwich assay or an immunochromatographic assay, containing a first molecule selected from the group consisting of BC2LCN, an antibody binding to SerpinA3, and an antibody binding to Gal3BP, and a second molecule that is BC2LCN, in which the kit can be used to measure an amount of a glycoprotein in a biological sample (for example, a blood sample) of a subject, using the first molecule and the second molecule. In one aspect of the kit of an embodiment of the present invention, the first molecule is immobilized on a substrate or strip and the second molecule is labeled. In one aspect of the kit of the embodiment of the present invention, the first molecule is labeled and the second molecule is immobilized on a substrate or strip. In some aspects, the first molecule is labeled and the second molecule is contained in or immobilized on the gel. The kit of an embodiment of the present invention may further contain a chromogenic substrate in a case where the label is an enzyme used in an enzyme-labeled antibody method. In a case where the biological sample is a blood sample, the component is a blood component.

In some aspects of the kit of the embodiment of the present invention, the first molecule is BC2LCN. In one aspect of the present invention, the first molecule is an antibody binding to SerpinA3. In one aspect of the present invention, the first molecule is an antibody binding to Gal3BP.

The kit of the embodiment of the present invention can be used in applications for detection of a target molecule, or for detection, determination, prediction, or diagnosis of a cancer.

According to the present invention, there is provided a combination of a first molecule selected from the group consisting of BC2LCN, an antibody binding to SerpinA3, and an antibody binding to Gal3BP, and a second molecule that is BC2LCN. The combination of the present invention can be used for detecting a component selected from the group consisting of a component that can simultaneously bind to two BC2LCN's, SerpinA3 bindable with BC2LCN, and Gal3BP bindable with BC2LCN in a sample (for example, a biological sample (for example, a blood sample)). In the combination, one of the first molecule and the second molecule may be immobilized on a support, and the other may be labeled for detection. The combination can be used to diagnose a cancer using a biological sample (for example, a blood sample). According to the present invention, there is provided a kit for diagnosing a cancer using a biological sample (for example, a blood sample) containing the combination. The combination may be a kit for a sandwich assay, a kit for an immunochromatographic assay, a kit for lectin electrophoresis, a kit for mass spectrometry, a kit for lectin affinity chromatography, or a kit for μTAS. The kit for lectin electrophoresis can contain a gel containing a lectin. The kit for lectin affinity chromatography can contain a column containing a support on which the lectin is immobilized. These kits may further contain purified SerpinA3, purified SerpinA3 bindable with BC2LCN, purified Gal3BP, or purified Gal3BP bindable with BC2LCN as a reference material. The kit for μTAS may contain a microfluidic chip. The microfluidic chip has a detection unit, and in the detection unit, a molecule to which one or more selected from the group consisting of SerpinA3, SerpinA3 bindable with BC2LCN, Gal3BP, Gal3BP bindable with BC2LCN, and a protein composite containing these bind can be immobilized.

According to the present invention, there is provided a method for analyzing a biological sample obtained from a subject, in which the method contains analyzing components (sometimes referred to as a "target component") contained in a biological sample by an assay using a first molecule selected from the group consisting of a molecule binding to a sugar chain bindable with BC2LCN, a molecule binding to SerpinA3, and a molecule binding to Gal3BP, and a second molecule that is BC2LCN can reduce a signal obtained by the assay by a reduction in a cancer in the body (for example, a removal of the cancer). Therefore, in the method of the embodiment of the present invention, the assay signal may indicate an amount of a cancer in the body. In addition, in the method, the signal obtained by the assay can be increased by relapse. Therefore, in the method of the embodiment of the present invention, the increased signal may indicate a relapse of a cancer.

According to the present invention, there is provided a method containing separating one or more components selected from the group consisting of a component that can simultaneously bind to two BC2LCN's, SerpinA3, and Gal3BP from a biological sample obtained from a subject. According to the present invention, there is provided a method containing detecting one or more components selected from the group consisting of a component that can simultaneously bind to two BC2LCN's, SerpinA3, and Gal3BP from a biological sample obtained from a subject.

According to the present invention, there is also provided a method for analyzing a biological sample obtained from a subject, in which the method contains separating one or more components selected from the group consisting of a component that can simultaneously bind to two BC2LCN's, SerpinA3, and Gal3BP in a biological sample obtained from a subject. The separation means separating a target component from at least one or more of the other components. The separation can contain concentration, enrichment, and purification of a target component. The concentration means increasing a concentration. The enrichment and the purification mean selectively increasing an abundance ratio of a target component to the other components. The enrichment and the purification may involve concentration of a target component. The separation can also contain binding to an immobilized molecule. In this case, the separation from the other components that do not bind to the immobilized molecule is performed by binding to the immobilized molecule. The separation may contain removing non-adsorbed components, in addition to adsorbing a target component to an immobilized surface. The non-adsorbed components can be removed by cleaning the surface. The removal of the non-adsorbed components can also be performed by removal of a liquid phase. The removal of the non-adsorbed components may also be performed by recovering beads in a case where a solid phase is present on the surface of the beads. In this aspect, the present invention may further contain measuring the amount of the separated components. The measurement can be performed by an assay known to a person skilled in the art, whereby assay signals can be obtained. The measured amount can be compared with other indicators (for example, a cut off value). The cut off value can be as described above.

In the method of the embodiment of the present invention, in a case where the measured amount is higher than others as an indicator, it can indicate that a subject from which a biological sample is derived has a potential to be a cancer. Therefore, the method of the embodiment of the present invention can be a method for detecting a cancer, a method for detecting a cancer cell, a method for diagnosing a cancer, a non-diagnostic method for diagnosing a cancer, a method for obtaining preliminary information for diagnosing a cancer, a method for predicting a cancer, or a non-diagnostic method for predicting a cancer. In the method of the embodiment of the present invention, a signal obtained by an assay can be reduced by reducing a cancer in the body (for example, removal of the cancer). Therefore, in the method of the embodiment of the present invention, the assay signal may indicate an amount of a cancer in the body. In addition, in the method, the signal obtained by the assay can be increased by relapse. Therefore, in the method of the embodiment of the present invention, the increased signal may indicate a relapse of a cancer. The method of the embodiment of the present invention can be performed on two or more biological samples recovered at different time points. Thus, in some aspects, the biological sample can be two or more biological samples recovered at different time points. In some aspects, the method of the embodiment of the present invention may further include comparing a signal obtained by an assay (corresponding to the measured amount) with a signal obtained in another sample that can be recovered at different time points. In this manner, the present invention can be used to monitor a cancer treatment process and/or relapse process of a patient.

The method of the embodiment of the present invention may be carried out in combination with an existing method. For example, as the existing method, a method containing measuring an amount of CA19-9 in a body fluid sample is known. CA19-9 has an increased concentration in a body fluid sample having a cancer. In addition, as the amount of the cancer increases, a concentration of CA19-9 in a body fluid sample increases, and as the amount of the cancer decreases, a concentration of CA19-9 decreases. Thus, the combination of CA19-9 and the method of the embodiment of the present invention can enhance an accuracy and/or specificity of cancer detection by the analysis of a body fluid sample. CA19-9 can be an indicator of a pancreatic cancer, in particular, a pancreatic cancer at a stage III, IV, or the like. Therefore, the present invention may further contain measuring a concentration of CA19-9 in a biological sample.

One or more components selected from the group consisting of SerpinA3 and Gal3BP to be measured may be further analyzed using those having a modification of a sugar chain bindable with BC2LCN as an indicator. Whether or not one or more components selected from the group consisting of SerpinA3 and Gal3BP have a modification of a sugar chain bindable with BC2LCN is determined by using a factor binding to the sugar modification (sugar chain) as described above. Alternatively, one or more components selected from the group consisting of SerpinA3 and Gal3BP may be detected after separation using a factor binding to the sugar modification (sugar chain). One or more components selected from the group consisting of SerpinA3 and Gal3BP may be detected after separation using a molecule binding to SerpinA3 and a molecule binding to Gal3BP.

EXAMPLES

Example 1: Detection of Glycoprotein in Sera of Cancer Patients Using rBC2LCN

Glycoproteins in the sera of patients with various cancers were detected by a sandwich assay with rBC2LCN.

First, biotinylated rBC2LCN was diluted with PBS to 0.3 μg/mL, added to an avidin plate (blocking-less type) (Sumitomo Bakelite Co., Ltd., BS-X7603) at 50 μL/well, and incubated at room temperature for 1 hour. The obtained rBC2LCN-immobilized plate was washed five times with PBS/0.1% Tween20 and then reacted with 50 μL/well (n=3) of the diluted sera of patients with various cancers diluted 100-fold with PBS. After the reaction at room temperature for 1 hour, the plate was washed five times with PBS/0.1% Tween20, 50 μL/well of an HRP-labeled rBC2LCN (1 μg/mL) was applied thereto, and a reaction was performed at room temperature for 1 hour. After washing five times with PBS/0.1% Tween20, 50 μL/well of a TMB solution (FUJIFILM Wako Pure Chemical Corporation) was applied, color was developed at room temperature for 30 minutes, 1 N HCl was reacted at 50 μL/well to stop the color developing reaction, and OD450/620 was measured. An average of the obtained numerical values is shown. The present sandwich assay with rBC2LCN indicates that the higher the value of OD450/620, the more a glycoprotein binding to rBC2LCN is present.

Figure 1:
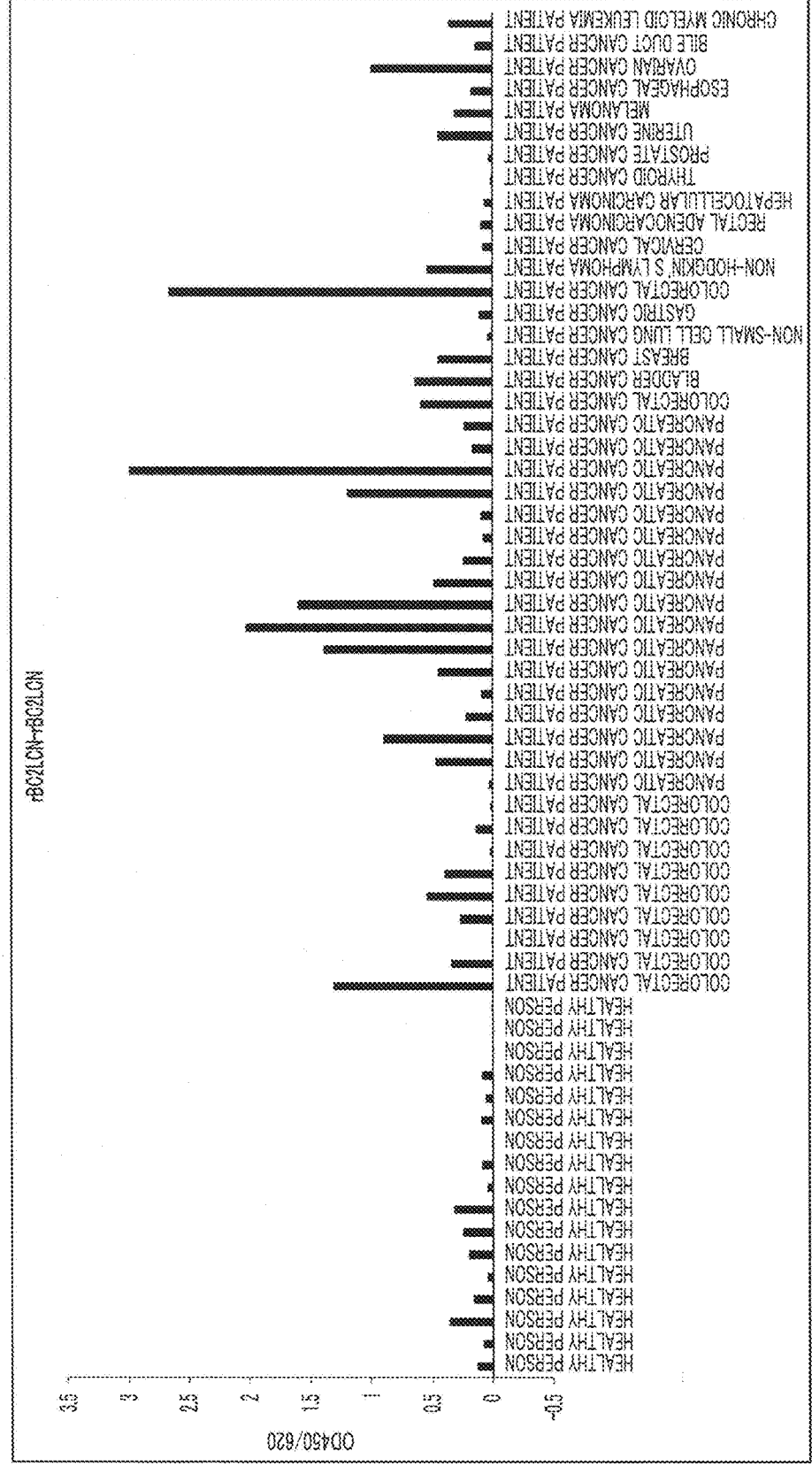
FIG. 1 shows the results of a sandwich assay, in which concentrations of blood factors that can be simultaneously recognized by two molecules of BC2LCN in blood samples of patients with various cancers and healthy persons were measured.
Figure 2:
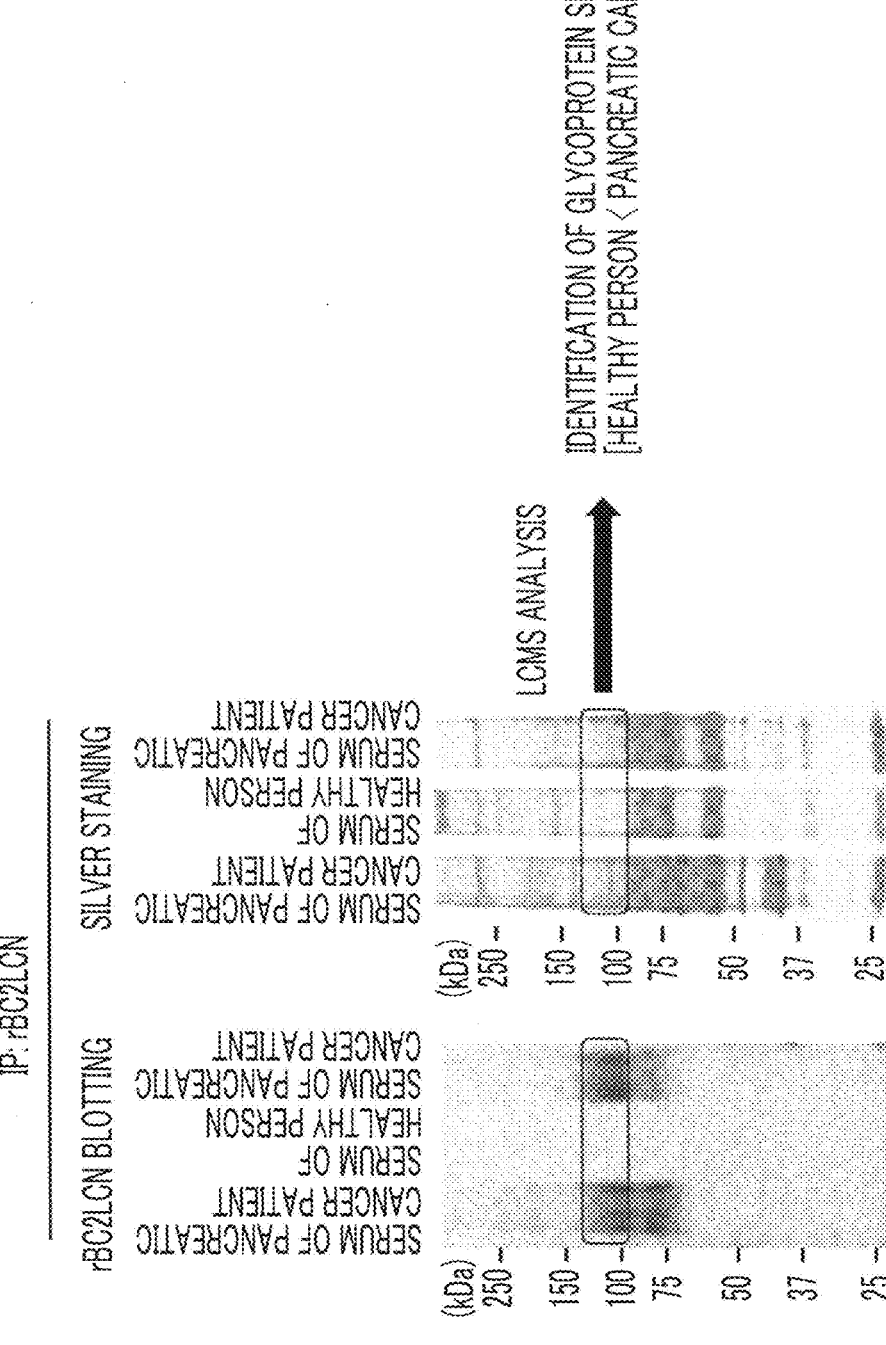
FIG. 2 shows the results of performing Western blotting using BC2LCN (left) and silver staining (right) by sedimenting blood components binding to BC2LCN, using BC2LCN from a blood sample, and then performing gel electrophoresis.

The results were as shown in FIG. 1. As shown in FIG. 1, it was revealed that glycoproteins detected by a sandwich assay with rBC2LCN in pancreatic cancer patients, colorectal cancer patients, bladder cancer patients, breast cancer patients, non-Hodgkin's lymphoma patients, uterine cancer patients, ovarian cancer patients, and chronic myeloid leukemia patients have higher concentrations than a maximum value observed in a group of healthy persons.

The detected glycoprotein must be able to simultaneously bind to two molecules of immobilized rBC2LCN and rBC2LCN for detection. From the results of the present Example, it was revealed that components that can simultaneously bind to two molecules of rBC2LCN (for example, blood components) are broader in cancer patients, have higher concentrations than healthy persons, and are thus useful for analysis of the components (for example, blood components).

Example 2: Identification of Glycoprotein Recognized by rBC2LCN

In the present Examples, glycoproteins in the sera of pancreatic cancer patients and healthy persons were each sedimented with rBC2LCN binding beads, the sedimented glycoproteins were eluted with rBC2LCN, the obtained eluates were electrophoresed, and glycoproteins unique to a pancreatic cancer were identified by mass spectrometry.

Biotinylated rBC2LCN was bound to Dynabeads M280 Streptavidin (Invitrogen). Then, the sera of pancreatic cancer patients and healthy persons were incubated overnight at 4° C. and washed, 0.2 M fucose was then added thereto, and incubation was performed at room temperature for 1 hour to elute glycoproteins bound to rBC2LCN. The obtained eluate was electrophoresed, transferred to a PVDF membrane, and then blotted with HRP-labeled rBC2LCN. As a result, no reactivity was observed in an rBC2LCN blot in the sera of the healthy persons, but a reactivity was observed in the vicinity of 75 to 150 kDa in the sera of the pancreatic cancer patients. Therefore, a portion surrounded by the red of 100 to 150 kDa was cut out from a gel stained with silver by electrophoresis. A peptide mixture was obtained from each of the cut gel pieces via trypsin hydrolysis. The peptide mixture was subjected to LC-MS/MS, and MS/MS data were obtained. The results of searching the amino acid sequence database of the MS/MS data were output as a peptide identification list. As a result, SerpinA3 and Gal3BP were obtained as candidate proteins to be detected in cancer patients by rBC2LCN.

Figure 3:
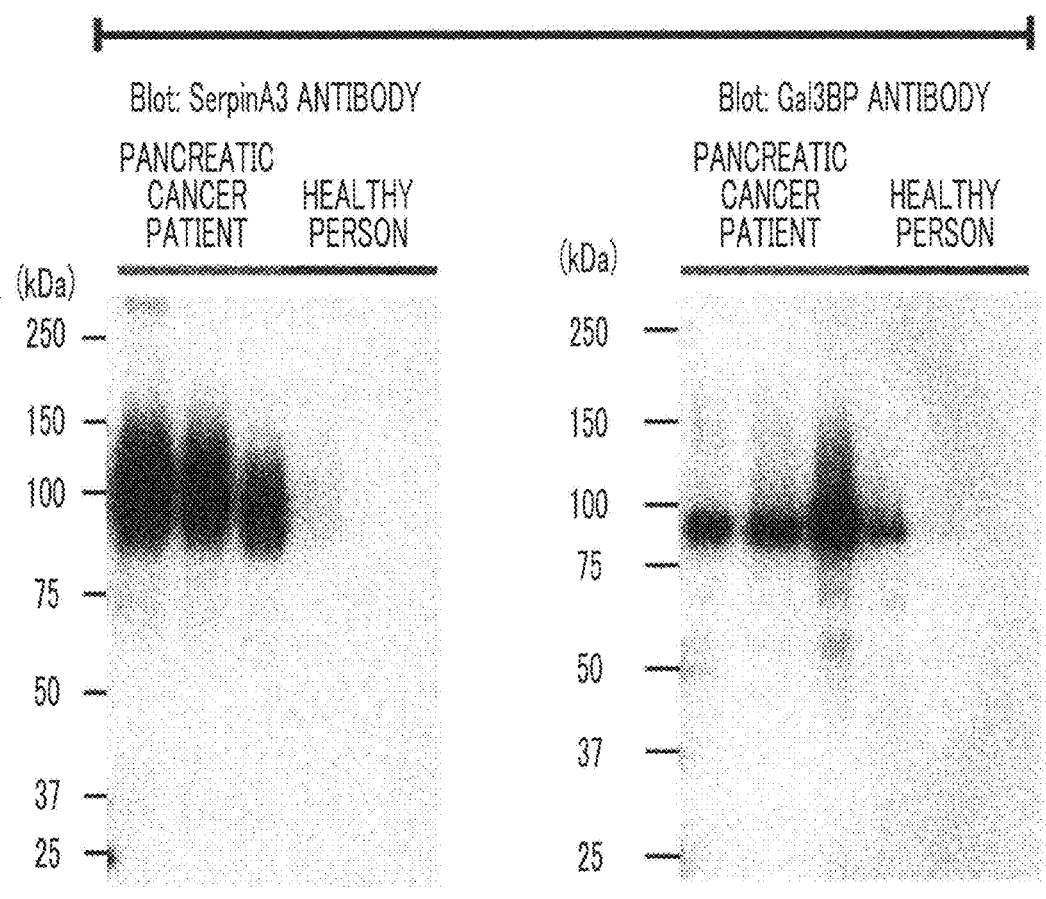
FIG. 3 shows the results of performing Western blotting using an antibody against SerpinA3 (left) and an antibody against Gal3BP (right) by sedimenting blood components binding to BC2LCN, using BC2LCN from a blood sample, and then performing gel electrophoresis.

Therefore, glycoproteins exhibiting bindability to rBC2LCN-immobilized beads were electrophoresed from the sera of the pancreatic cancer patients and the healthy persons, and subjected to Western blots using an antibody against SerpinA3, an antibody against Gal3BP, and an HRP-labeled secondary antibody. As a result, as shown in FIG. 3, SerpinA3 and Gal3BP were detected significantly more strongly in the sera of the pancreatic cancer patients, as compared with those in the healthy persons. Since SerpinA3 and Gal3BP were obtained as proteins adsorbed on beads by rBC2LCN, it was found that these glycoproteins are reactive to rBC2LCN.

Normal pancreatic tissues and pancreatic cancer tissues were obtained from patients, and subjected to immunohistochemical staining. The immunohistochemical staining was performed according to an ordinary method. As a primary antibody, an anti-SerpinA3 antibody (manufactured by R & D Systems, Inc., product number: MAB12945, dilution ratio: 200 times) was used for staining of SerpinA3, and an anti-Gal3BP antibody (manufactured by R & D Systems, Inc.) was used for staining of Gal3BP, product number: AF2226, 1 μg/mL). In addition, as a secondary antibody, biotinylated anti-mouse IgG (manufactured by Nichirei Bioscience, Inc., product number: 424021, dilution ratio: stock solution) and biotinylated anti-goat IgG (manufactured by Nichirei Bioscience, Inc., product number: 414011, dilution ratio: stock solution) were each used. The results were as shown in FIG. 9. As shown in FIG. 9, it was revealed that in the normal pancreatic tissues, a stained image was hardly observed, whereas in the pancreatic cancer tissues, SerpinA3 and Gal3BP were strongly expressed in the pancreatic duct.

It is suggested that SerpinA3 and Gal3BP detected in the blood are derived from the pancreatic duct of the pancreatic cancer tissue.

Example 3: Analysis of Sera of Cancer Patients in Sandwich Assay Using rBC2LCN and SerpinA3 Antibody or Gal3BP Antibody Therefore, a sandwich assay of rBC2LCN and a SerpinA3 antibody was constructed, and the sera of the healthy persons and the patients with various cancers containing a pancreatic cancer were analyzed. Biotinylated rBC2LCN was diluted with PBS to 0.3 μg/mL, added to an avidin plate (blocking-less type) (Sumitomo Bakelite Co., Ltd., BS-X7603) at 50 μL/well, and incubated at room temperature for 1 hour. The obtained rBC2LCN-immobilized plate was washed five times with PBS/0.1% Tween20 and then reacted with 50 μL/well (n=3) of the diluted sera of patients with various cancers diluted 100-fold with PBS. After the reaction at room temperature for 1 hour, the plate was washed five times with PBS/0.1% Tween20, 50 μL/well of an HRP-labeled SerpinA3 antibody (1 μg/mL; R & D Systems, Inc., Cat #: AF1295) was applied thereto, and a reaction was performed at room temperature for 1 hour. After washing five times with PBS/0.1% Tween20, 50 μL/well of a TMB solution (FUJIFILM Wako Pure Chemical Corporation) was applied, color was developed at room temperature for 30 minutes, 1N HCl was reacted at 50 μL/well to stop the color developing reaction, and OD450/620 was measured. An average of the obtained numerical values is shown.

Figure 4:
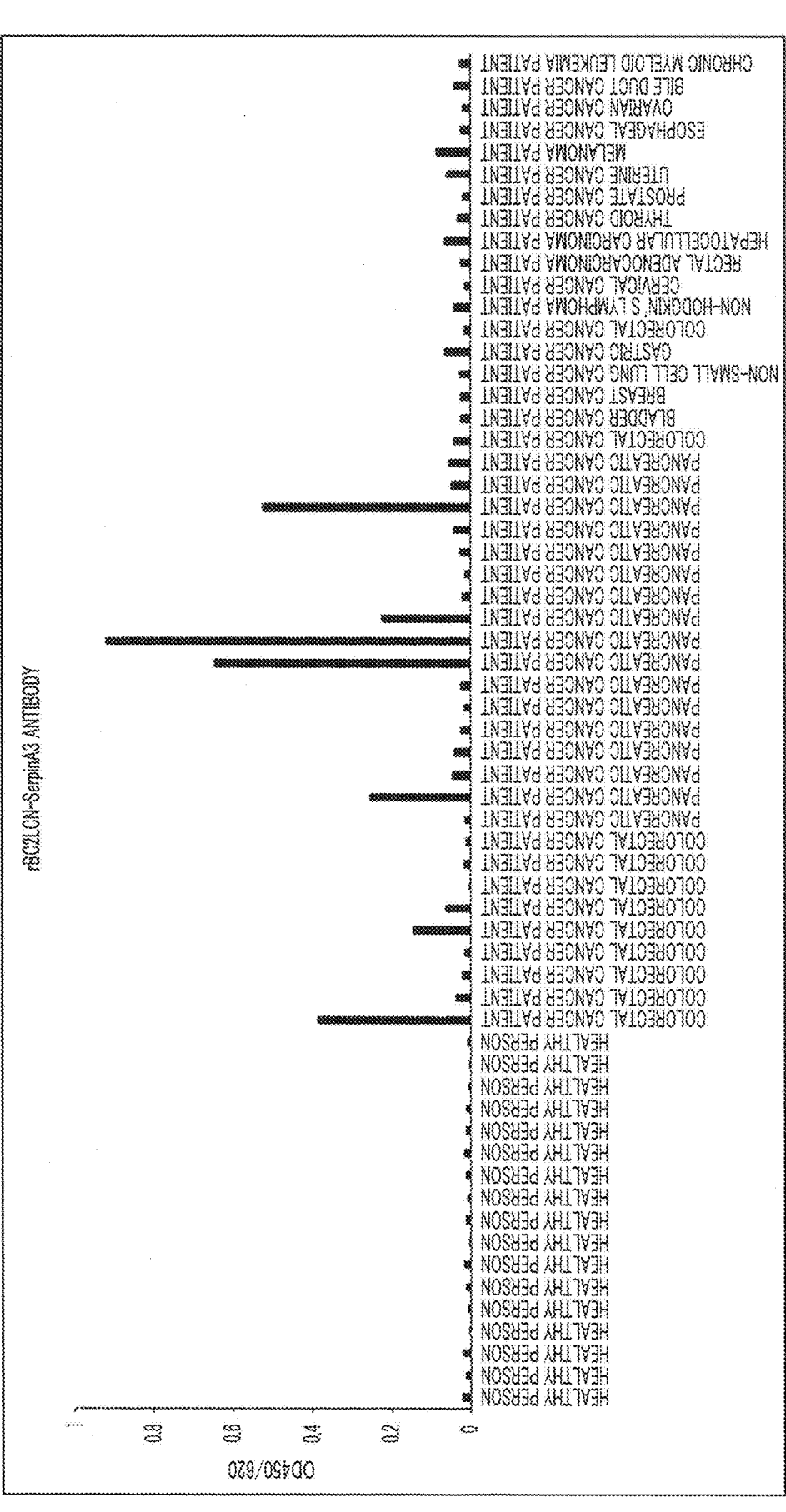
FIG. 4 shows the results of performing a sandwich assay using BC2LCN and an antibody binding to SerpinA3 in blood samples of patients with various cancers and healthy persons.

The results were as shown in FIG. 4. As shown in FIG. 4, the glycoprotein (that is, SerpinA3 having a specific sugar chain binding to a BC2LCN lectin) detected by a sandwich assay of rBC2LCN and a SerpinA3 antibody could hardly be detected in healthy persons, whereas the glycoprotein was strongly detected in all of a colorectal cancer, a pancreatic cancer, a bladder cancer, a gastric cancer, a small cell lung cancer, a breast cancer, a non-Hodgkin's lymphoma, a cervical cancer, a rectal adenocarcinoma, a hepatocellular carcinoma, a thyroid cancer, a prostate cancer, a uterine cancer, a melanoma, an esophageal cancer, an ovarian cancer, a bile duct cancer, and a chronic myeloid leukemia (all of the cancers examined).

Next, a sandwich assay of rBC2LCN and a Gal3BP antibody was constructed, and the sera of the healthy persons and the patients with various cancers containing a pancreatic cancer were analyzed. Biotinylated rBC2LCN was diluted with PBS to 0.3 μg/mL, added to an avidin plate (blocking-less type) (Sumitomo Bakelite Co., Ltd., BS-X7603) at 50 μL/well, and incubated at room temperature for 1 hour. The obtained rBC2LCN-immobilized plate was washed five times with PBS/0.1% Tween20 and then reacted with 50 μL/well (n=3) of the diluted sera of patients with various cancers diluted 100-fold with PBS. After the reaction at room temperature for 1 hour, the plate was washed five times with PBS/0.1% Tween20, 50 μL/well of an HRP-labeled Gal3BP antibody (1 μg/mL; R & D Systems, Inc., Cat #: AF2226) was applied thereto, and a reaction was performed at room temperature for 1 hour. After washing five times with PBS/0.1% Tween20, 50 μL/well of a TMB solution (FUJIFILM Wako Pure Chemical Corporation) was applied, color was developed at room temperature for 30 minutes, 1 N HCl was reacted at 50 μL/well to stop the color developing reaction, and OD450/620 was measured. A graph was created by averaging the obtained numerical values. An average of the obtained numerical values is shown.

Figure 5:
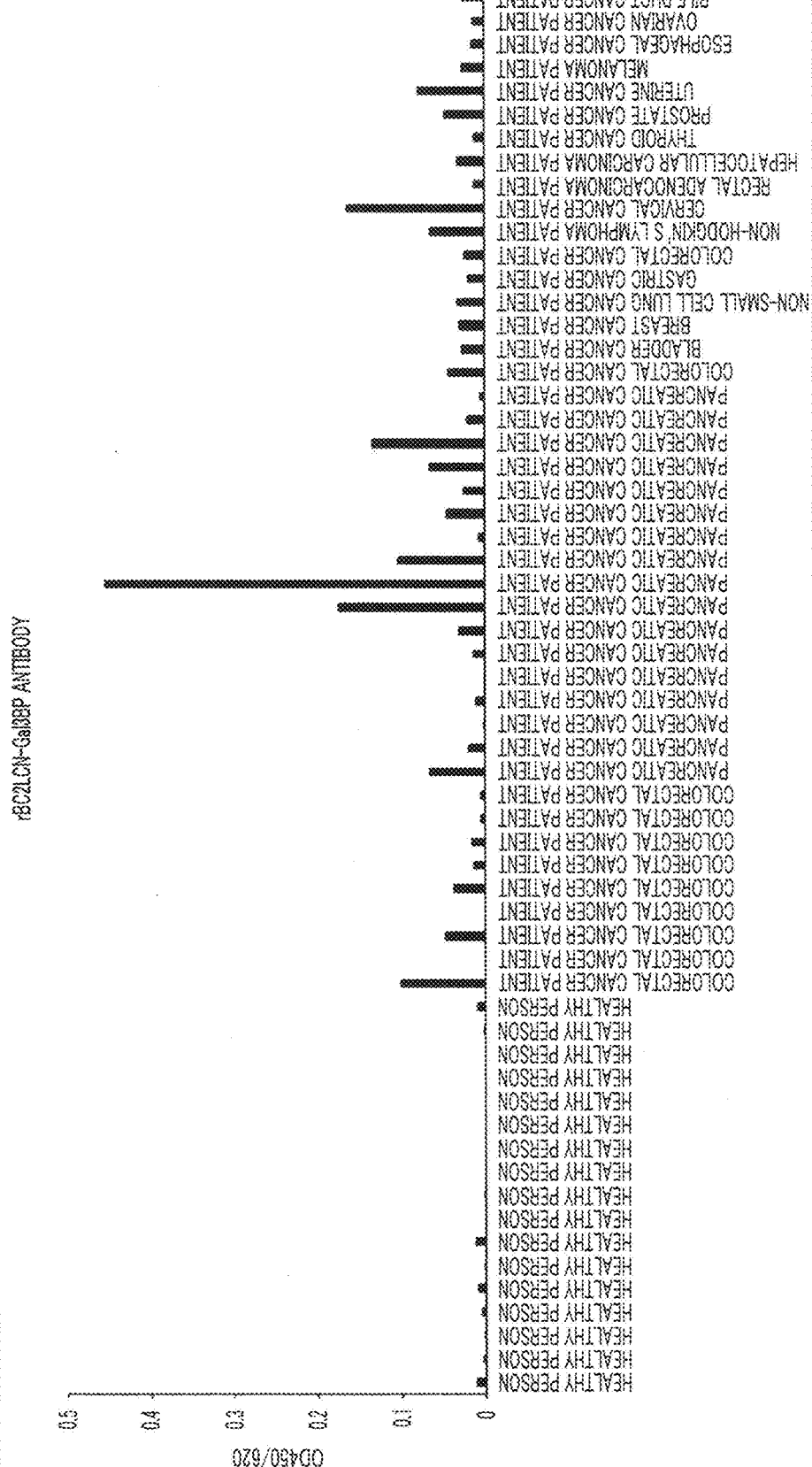
FIG. 5 shows the results of performing a sandwich assay using BC2LCN and an antibody binding to Gal3BP in blood samples of patients with various cancers and healthy persons.

The results were as shown in FIG. 5. As shown in FIG. 5, the glycoprotein (that is, Gal3BP having a specific sugar chain binding to a BC2LCN lectin) detected by a sandwich assay of rBC2LCN and a Gal3BP antibody can hardly be detected in healthy persons, whereas the glycoprotein was strongly detected in all of a colorectal cancer, a pancreatic cancer, a bladder cancer, a gastric cancer, a small cell lung cancer, a breast cancer, a non-Hodgkin's lymphoma, a cervical cancer, a rectal adenocarcinoma, a hepatocellular carcinoma, a thyroid cancer, a prostate cancer, a uterine cancer, a melanoma, an esophageal cancer, an ovarian cancer, a bile duct cancer, and a chronic myeloid leukemia (all of the cancers examined).

In addition, in FIG. 10, a comparison was made separately for healthy persons, pancreatitis patients, and pancreatic cancer patients. As a result, in a sandwich assay of rBC2LCN and rBC2LCN, a sandwich assay of rBC2LCN and an anti-SerpinA3 antibody, a sandwich assay of rBC2LCN and an anti-Gal3BP antibody, and a sandwich assay of an anti-SerpinA3 antibody and an anti-SerpinA3 antibody, stronger signals were detected with the pancreatic cancer patients, as compared to those with the healthy persons and those with pancreatitis. This suggests that these assays can distinguish pancreatic cancer patients from healthy persons or pancreatitis patients.

From this, it was revealed that SerpinA3 having a specific sugar chain binding to a BC2LCN lectin and Gal3BP having a specific sugar chain binding to a BC2LCN lectin are widely present in the serum of cancer patients.

Furthermore, a sandwich assay with rBC2LCN and rBC2LCN, a sandwich assay with rBC2LCN and an anti-SerpinA3 antibody, a sandwich assay with rBC2LCN and an anti-Gal3BP antibody, and a sandwich assay with an anti-SerpinA3 antibody (R & D Systems, Inc., Cat #: AF1295) and anti-SerpinA3 antibody (R & D Systems, Inc., Cat #: AF1295) were performed by the method as described above, using serum specimens from other healthy persons and serum specimens from pancreatic cancer patients.

Figure 6:
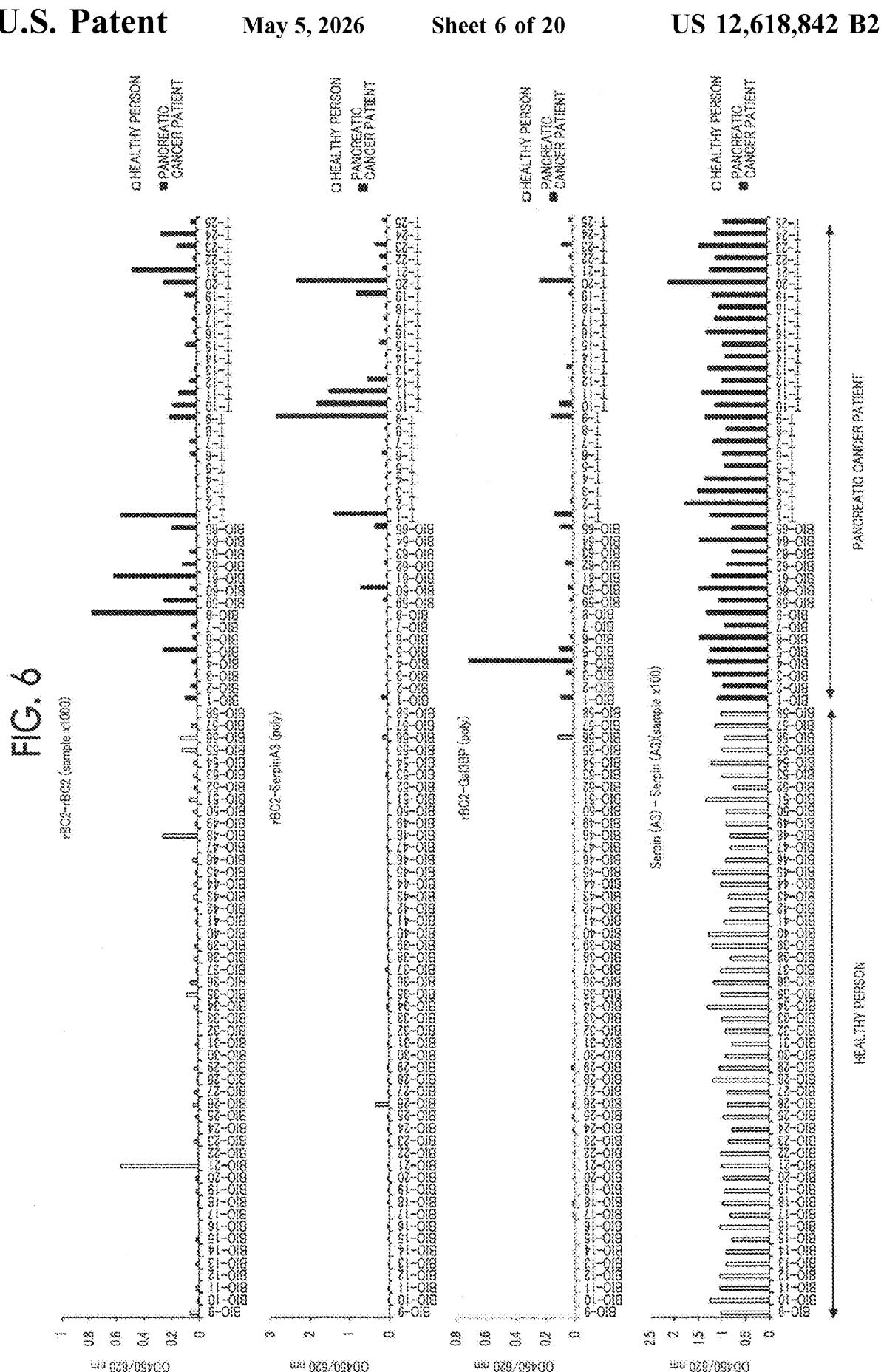
FIG. 6 shows the results of a concentration of blood factors that can be simultaneously recognized by two molecules of BC2LCN, a concentration of SerpinA3 bindable with BC2LCN, a concentration of Gal3BP bindable with BC2LCN, and a concentration of SerpinA3 measured using two different anti-SerpinA3 antibodies in blood samples of pancreatic cancer patients and healthy persons.

The results were as shown in FIG. 6. As shown in FIG. 6, in a sandwich assay with rBC2LCN and rBC2LCN, a sandwich assay with rBC2LCN and an anti-SerpinA3 antibody, and the sandwich assay with rBC2LCN and an anti-Gal3BP antibody, higher measuring intensities were obtained in the sandwich assay with the sera of the pancreatic cancer patients rather than the sera of the healthy persons. On the other hand, in a sandwich assay with the anti-SerpinA3 antibody and the anti-SerpinA3 antibody, the measured intensities were the same in the sera of both the healthy persons and the pancreatic cancer patients. This is a result suggesting that SerpinA3 is present in the sera of both the healthy persons and the pancreatic cancer patients, but in the pancreatic cancer patients, SerpinA3 is specifically modified with a sugar recognizable by rBC2LCN.

The results obtained above were analyzed, and an ROC curve was drawn with a specificity as the horizontal axis and a sensitivity as the vertical axis. The results were as shown in FIG. 7.

Figure 7:
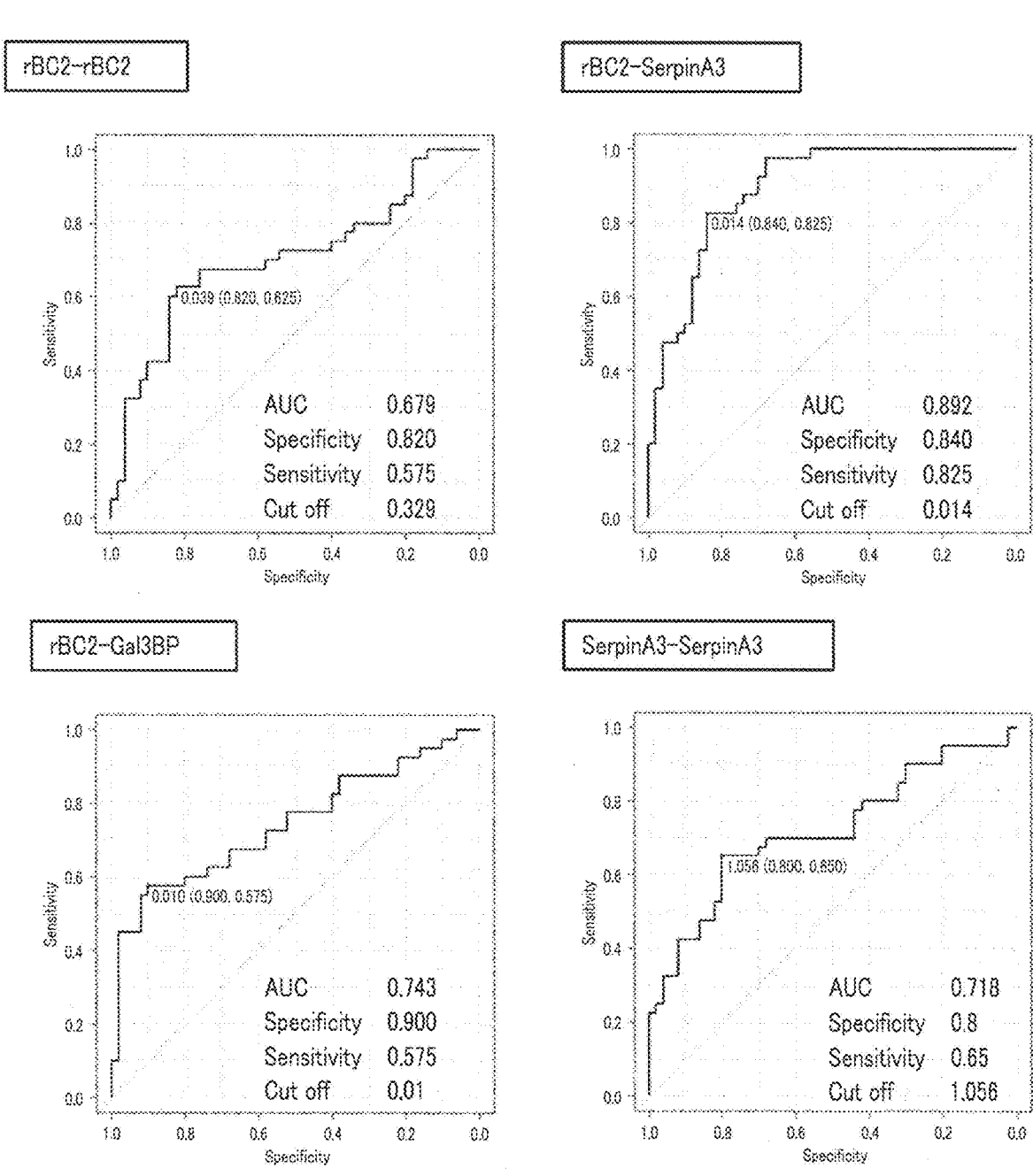

As shown in the upper left panel of FIG. 7, in the sandwich assay (rBC2-rBC2) using rBC2LCN and rBC2LCN, the area under the ROC curve (AUC) was 0.679, the cut off on the ROC curve (determined from a point on the ROC curved line at the shortest distance from a sensitivity of 1 and a specificity of 1) was 0.329, at which the specificity and the sensitivity were 0.820 and 0.575, respectively.

As shown in the upper right panel of FIG. 7, in the sandwich assay (rBC2-SerpinA3) using rBC2LCN and an anti-SerpinA3 antibody, the area under the ROC curve (AUC) was 0.892, and the cut off on the ROC curve (determined from a point on the ROC curved line at the shortest distance from a sensitivity of 1 and a specificity of 1) was 0.014, at which the specificity and the sensitivity were 0.840 and 0.825, respectively.

As shown in the lower left panel of FIG. 7, in the sandwich assay (rBC2-Gal3BP)) using rBC2LCN and an anti-Gal3BP antibody, the area under the ROC curve (AUC) was 0.743, and the cut off on the ROC curve (determined from a point on the ROC curved line at the shortest distance from a sensitivity of 1 and a specificity of 1) was 0.01, at which the specificity and the sensitivity were 0.900 and 0.575, respectively.

Furthermore, as shown in the lower right panel of FIG. 7, in the sandwich assay (SerpinA3-SerpinA3) with an anti-SerpinA3 antibody and an anti-SerpinA3 antibody, the area under the ROC curve (AUC) was 0.718, and the cut off on the ROC curve (determined from a point on the ROC curved line at the shortest distance from a sensitivity of 1 and a specificity of 1) was 1.056, at which the specificity and the sensitivity were 0.8 and 0.65, respectively.

From the results, it was revealed that the sandwich assay (rBC2-SerpinA3) with rBC2LCN and an anti-SerpinA3 antibody has the most excellent accuracy, and the sandwich assay (rBC2-Gal3BP) with rBC2LCN and an anti-Gal3BP antibody exhibits the mot excellent specificity. In addition, it was revealed that the sandwich assay (rBC2-rBC2) with rBC2LCN and rBC2LCN, and the sandwich assay (SerpinA3-SerpinA3) with an anti-SerpinA3 antibody and an anti-SerpinA3 antibody also show an accuracy with a certain usefulness.

Furthermore, a ROC curve was created and examined whether or not healthy persons (n=49) and pancreatitis patients (n=9) could be distinguished from pancreatic cancer patients (n=85). Then, as shown in FIG. 11, it was revealed that the sandwich assay (rBC2-SerpinA3) with rBC2LCN and an anti-SerpinA3 antibody and the sandwich assay (rBC2-Gal3BP) with rBC2LCN and an anti-Gal3BP antibody exhibit the mot excellent AUC. In addition, it was revealed that the sandwich assay (rBC2-rBC2) with rBC2LCN and rBC2LCN, and the sandwich assay (SerpinA3-SerpinA3) with an anti-SerpinA3 antibody and an anti-SerpinA3 antibody also have constant usefulness.

Example 5: Analysis of Sera of Pancreatic Cancer Patients for Each Stage

In the present Example, serum specimens of patients with various pancreatic cancers from a stage IA to a stage IV were evaluated by a sandwich assay.

The stage of the cancer was determined by a doctor, based on a UICC TNM classification (UICC: TNM Classification of Malignant Tumors, 8th Edn. Wiley-Blackwell; 2017. 94-95). As described in Examples 1 and 3, the sera of the cancer patients were each subjected to a sandwich assay with rBC2LCN and rBC2LCN, a sandwich assay with rBC2LCN and an anti-SerpinA3 antibody, a sandwich assay with rBC2LCN and an anti-Gal3BP antibody, and a sandwich assay with an anti-SerpinA3 antibody and an anti-SerpinA3 antibody. The results were as shown in FIGS. 8A to 8D.

As shown in FIGS. 8A to 8C, in the sandwich assay with rBC2LCN and rBC2LCN, the sandwich assay with rBC2LCN and an anti-SerpinA3 antibody, and the sandwich assay with rBC2LCN and an anti-Gal3BP antibody, samples having high measuring intensities were confirmed at all of stages I to IV.

As shown in FIG. 8D, in the sandwich assay with an anti-SerpinA3 antibody and an anti-SerpinA3 antibody, all the samples showed high measuring intensities as shown in FIG. 6.

An ROC curve was created between stage I pancreatic cancer patients (n=9) and healthy persons (n=49). The results were as shown in FIG. 12. As shown in FIG. 12, the stage I pancreatic cancer patients were successfully detected in both the sandwich assays. An ROC curve was created between stage II pancreatic cancer patients (n=51) and healthy persons (n=49). The results were as shown in FIG. 13. As shown in FIG. 13, the stage II pancreatic cancer patients were successfully detected in both the sandwich assays. A ROC curve was created between stage III pancreatic cancer patients (n=8) and healthy persons (n=49). The results were as shown in FIG. 14. As shown in FIG. 14, the stage III pancreatic cancer patients were successfully detected in any of the sandwich assays shown. An ROC curve was created between stage IV pancreatic cancer patients (n=17) and healthy persons (n=49). The results were as shown in FIG. 15. As shown in FIG. 15, stage IV pancreatic cancer patients were successfully detected in any of the sandwich assays shown.

An operation to remove a pancreatic cancer was carried out for the pancreatic cancer patients. Preoperative and postoperative blood samples (n=38) were analyzed by an sandwich assay. The results of the sandwich assay with rBC2LCN and an anti-SerpinA3 antibody are shown in FIG. 16, the results of the sandwich assay with rBC2LCN and an anti-Gal3BP antibody are shown in FIG. 17, and the results of the CA19-9 assay are shown in FIG. 18. In each of the figures, 30 POD means 30 days after the operation and 3 m means 3 months after the operation. As shown in FIGS. 16 to 18, the signal for each sandwich assay was reduced by an operation to remove the cancer. Therefore, in these assays, it can be seen that the outcome of the removal of a cancer affects a content of components in the blood.

In addition, blood samples of patients with relapses were assayed over time. The assay was a sandwich assay using BC2LCN and an anti-SerpinA3 antibody. The results were as shown in FIG. 19. As shown in FIG. 19, in patients A, the assay signal decreased over time after the operation. However, analysis of the blood of the patients A who had relapsed showed a remarkable increase in the signal. This suggests that the assay system of the present invention can be used for detecting a relapse.

Therefore, in the sandwich assay with rBC2LCN and rBC2LCN, the sandwich assay with rBC2LCN and an anti-SerpinA3 antibody, and the sandwich assay with rBC2LCN and an anti-Gal3BP antibody, a wide range of cancers from early stage pancreatic cancers such as a stage I cancer and a stage II cancer to a stage IV pancreatic cancer can be detected by appropriately setting the cut off values.

The invention claimed is:

1. A method for detecting components in a biological sample obtained from a subject, comprising:
   contacting the sample with a first molecule that is an antibody binding to SerpinA3 or an antibody binding to Gal3BP, and with a second molecule that is BC2LCN, and
   detecting binding of the first and second molecules to the components in the sample.

2. The method according to claim 1,
wherein the subject has a cancer or has a potential to have the cancer.

3. The method according to claim 2,
wherein the subject has a pancreatic cancer or has a potential to have the pancreatic cancer.

4. The method according to claim 3,
wherein the subject has a stage I or II pancreatic cancer or has a potential to have the stage I or II pancreatic cancer.

\* \* \* \* \*